US008598216B1

(12) United States Patent
Acquasaliente et al.

(10) Patent No.: US 8,598,216 B1
(45) Date of Patent: Dec. 3, 2013

(54) RITONAVIR BIS-HYDROCHLORIDE

(75) Inventors: Maurizio Acquasaliente, Kent (GB);
Didier Houllemare, West Malling (GB);
Geoff Zhang, Vernon Hills, IL (US);
Pulla Singam, Northbrook, IL (US);
John Morris, Grayslake, IL (US);
Kennan Marsh, Lake Forest, IL (US);
Martin Babcock, Pleasant Prairie, WI
(US); John Pavlina, Pleasant Prairie, WI
(US); Yi Shi, Libertyville, IL (US);
Yuchuan Gong, Waukegan, IL (US)

(73) Assignee: Abbvie Inc., North Chicago, IL (US)

( * ) Notice: Subject to any disclaimer, the term of this patent is extended or adjusted under 35 U.S.C. 154(b) by 0 days.

(21) Appl. No.: 13/328,043

(22) Filed: Dec. 16, 2011

Related U.S. Application Data

(60) Provisional application No. 61/424,307, filed on Dec. 17, 2010.

(51) Int. Cl.
*A61K 31/426* (2006.01)
*A61K 31/41* (2006.01)

(52) U.S. Cl.
USPC .......................... 514/365; 514/183; 514/359

(58) Field of Classification Search
USPC ......................................... 514/183, 359, 365
See application file for complete search history.

(56) References Cited

U.S. PATENT DOCUMENTS 5,674,882 A * 10/1997 Kempf et al. ................. 514/365
6,232,333 B1 * 5/2001 Lipari et al. ................. 514/365
6,407,252 B1 * 6/2002 Bellani et al. ................ 548/203

OTHER PUBLICATIONS

Bellamy L.J., ed., "The Infrared Spectra of Complex Molecules" in: Advances in Infrared Group Frequencies, vol. 2, Second Edition, Chapman and Hall Ltd., New York, 1980, Table of Contents.
Brown J.H., et al., "Muscarinic Receptor Agonists and Antagonists" in: The Pharmacological Basis of Therapeutics, 10th Edition, Goodman & Gilman. ed., McGraw-Hill Publications, 2001, Chap. 7, pp. 155-173.
Colthup N.B., et al., "Introduction to Infrared and Raman Spectroscopy," 3rd Edition, Harcourt Brace Jovanovich, Publishers, Academic Press, Inc., San Diego, 1990, Table of Contents.
Gennaro A.R., ed., Remington's Pharmaceutical Sciences, 18th Edition, Mack Publishing Company, 1990, Table of Contents.
Law D., et al., "Physicochemical Considerations in the Preparation of Amorphous Ritonavir-Poly(ethylene Glycol) 8000 Solid Dispersions," Journal of Pharmaceutical Sciences, 2001, vol. 90(8), pp. 1015-1025.
Lin-Vien D., et al., "The Handbook of Infrared and Raman Characteristic Frequencies of Organic Molecules," Harcourt Brace Jovanovich, Publishers, Academic Press, Inc., San Diego, 1991, Table of Contents.
Socrates G., "Infrared and Raman Characteristic Group Frequencies" in: Tables and Charts, 3rd Edition, John Wiley and Sons, Ltd., New York, 2001, Table of Contents.
Charts, 3rd Edition, John Wiley and Sons, Ltd., New York, 2001, Table of Contents.

* cited by examiner

*Primary Examiner* — My-Chau T Tran
(74) *Attorney, Agent, or Firm* — J.A. Lindeman & Co., PLLC

(57) ABSTRACT

The invention relates to ritonavir bis-hydrochloride, processes for the preparation of the ritonavir bis-hydrochloride, pharmaceutical compositions containing the ritonavir bis-hydrochloride and made from it, and methods of using the ritonavir bis-hydrochloride to inhibit HIV protease or enhance the pharmacokinetics of compounds which are metabolized by cytochrome $P_{450}$ 3A4.

18 Claims, 11 Drawing Sheets
(9 of 11 Drawing Sheet(s) Filed in Color)

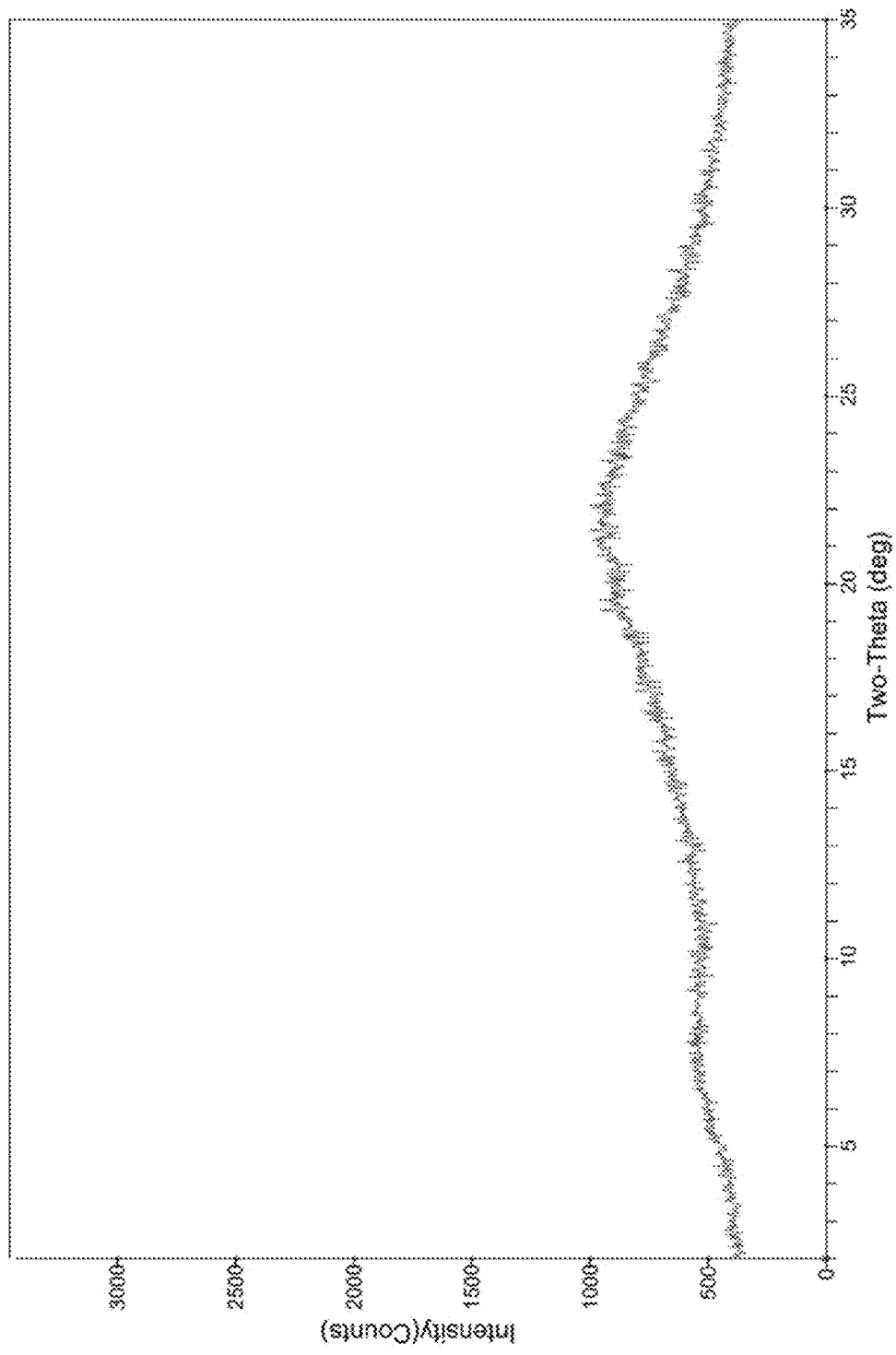

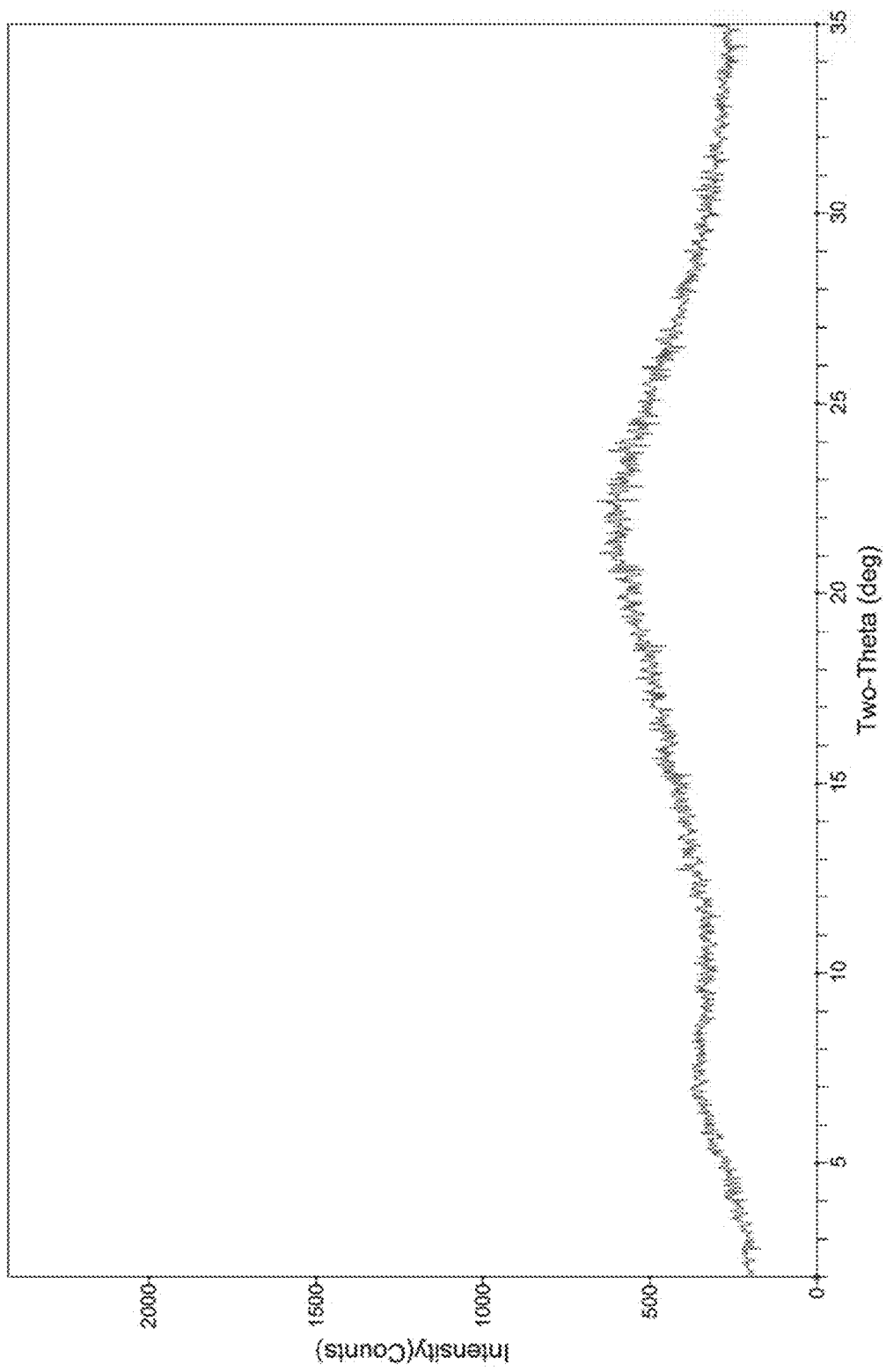
Figure 2: XRPD of Large-scale Amorphous Ritonavir Bis-Hydrochloride

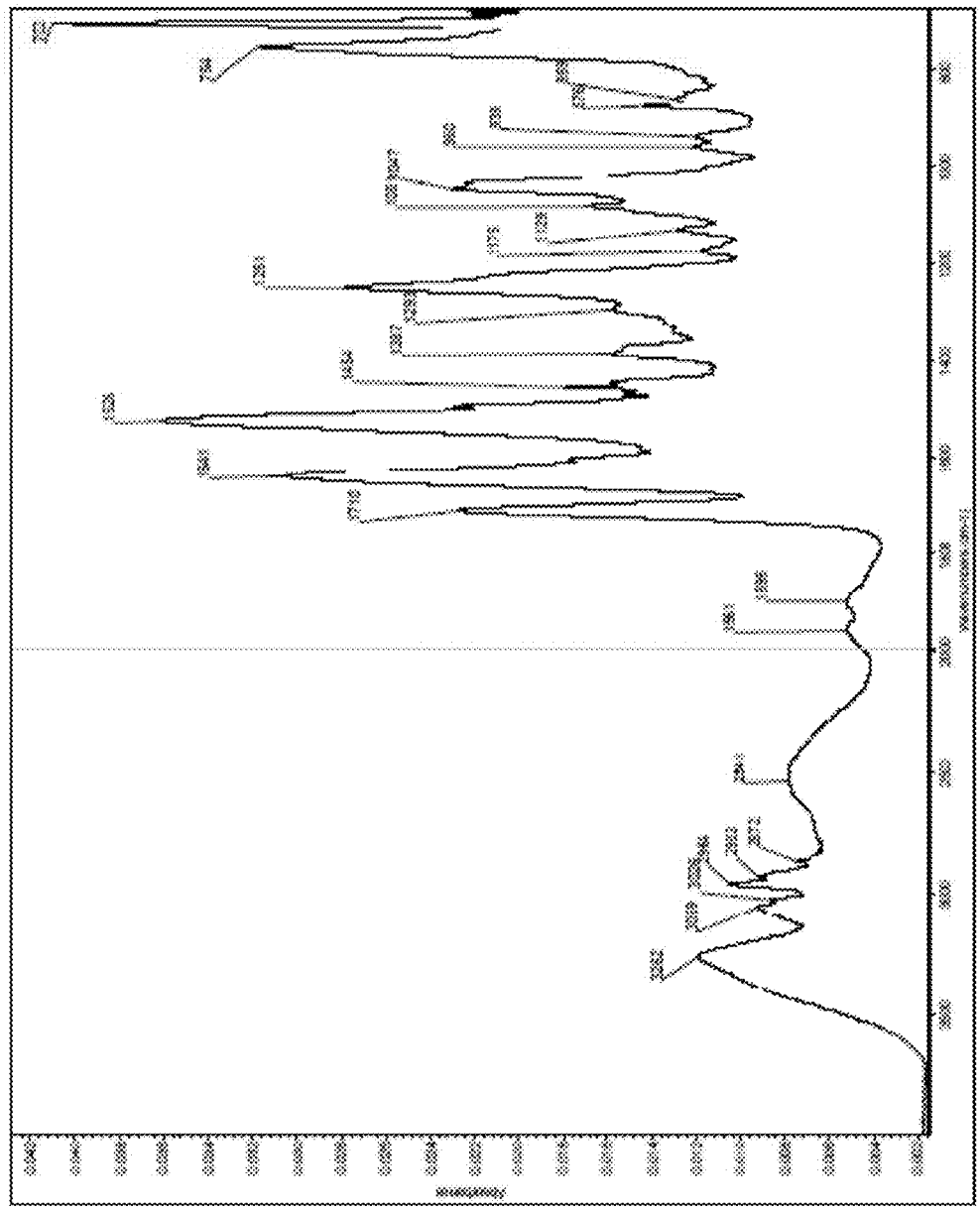

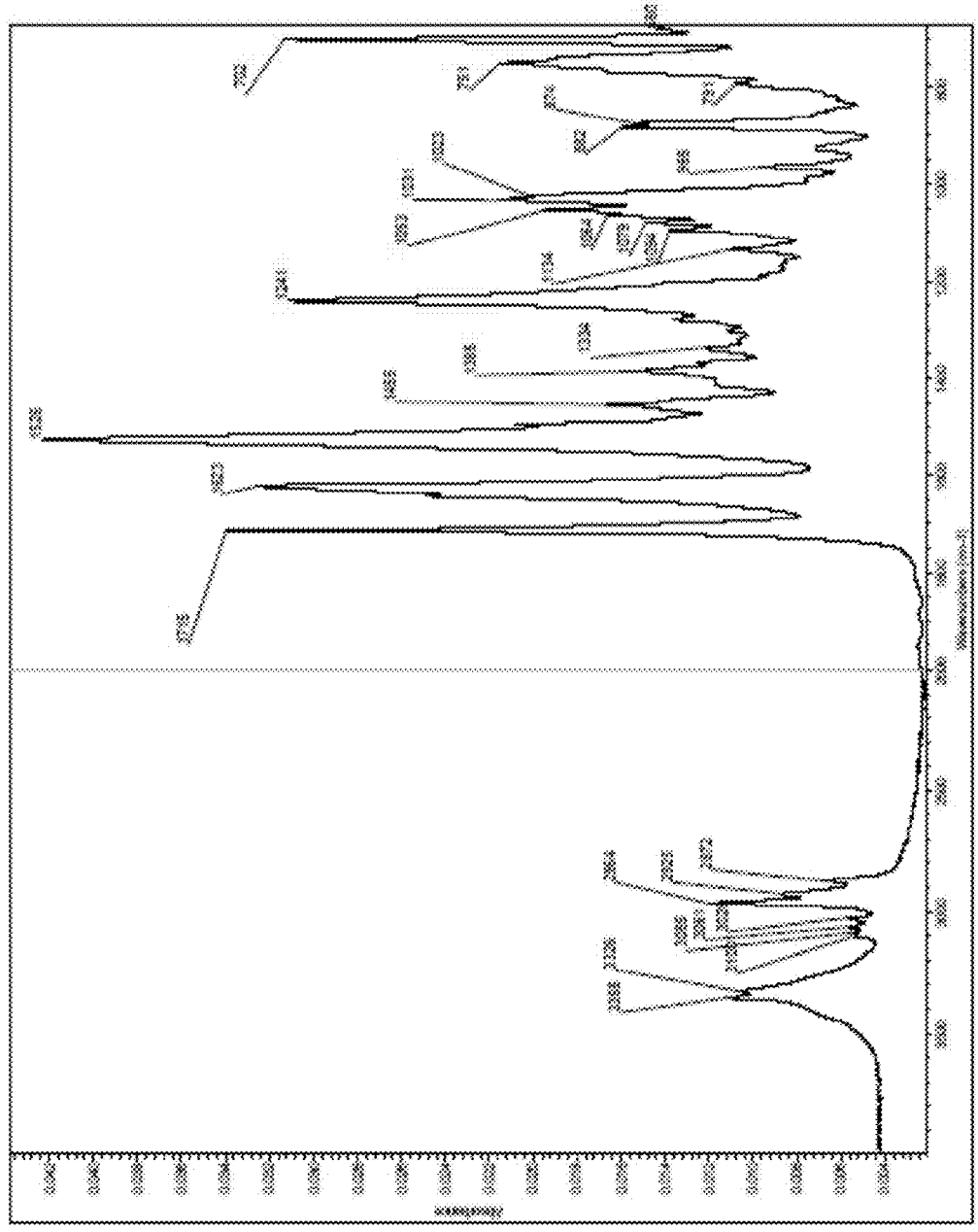
Figure 4: Infrared Spectrum of Amorphous Ritonavir Free Base

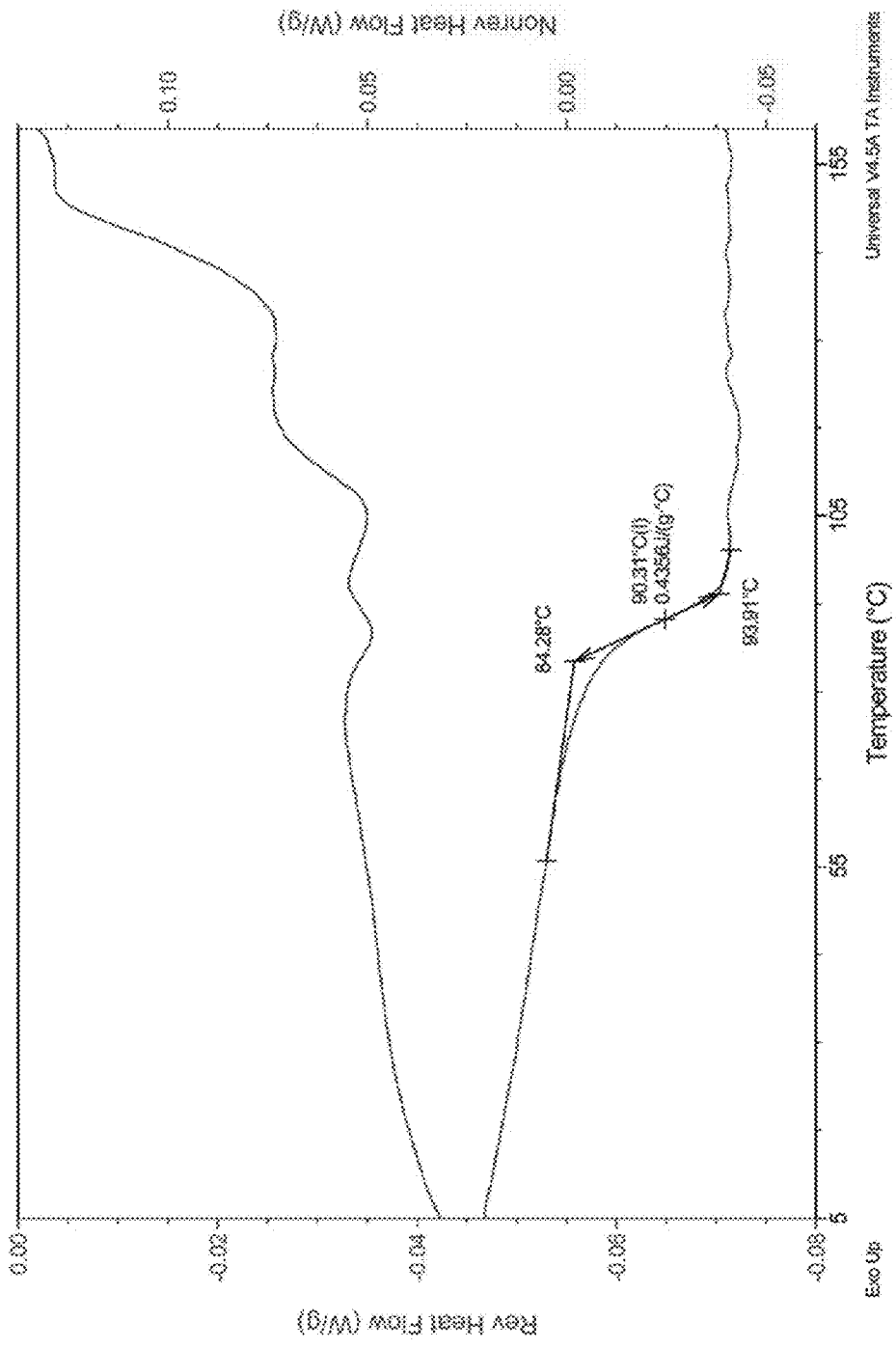
Figure 5: DSC of Large-scale Amorphous Ritonavir Bis-Hydrochloride
Green Curve = Reversible Heat Low; Blue Curve = Irreversible Heat Flow

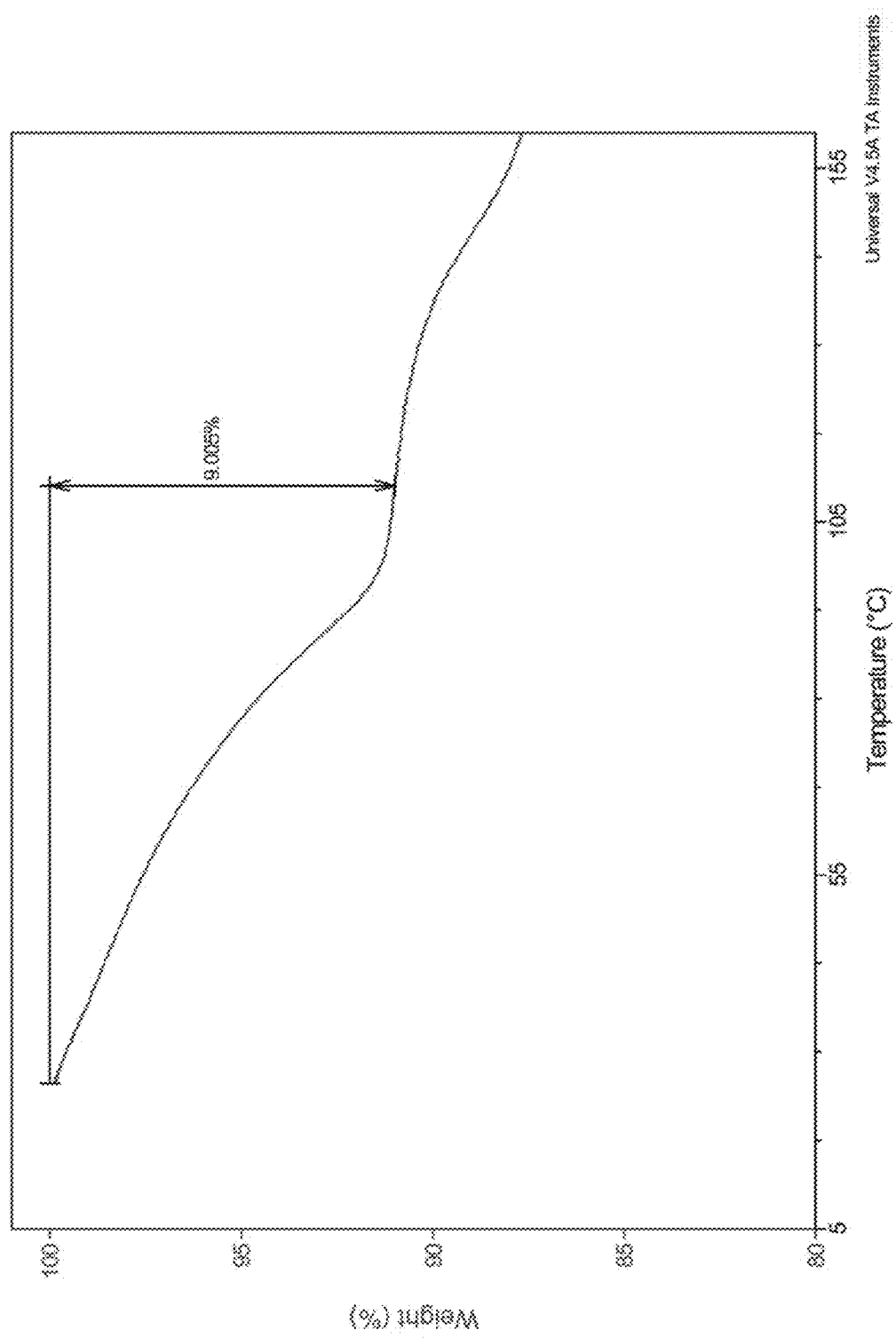

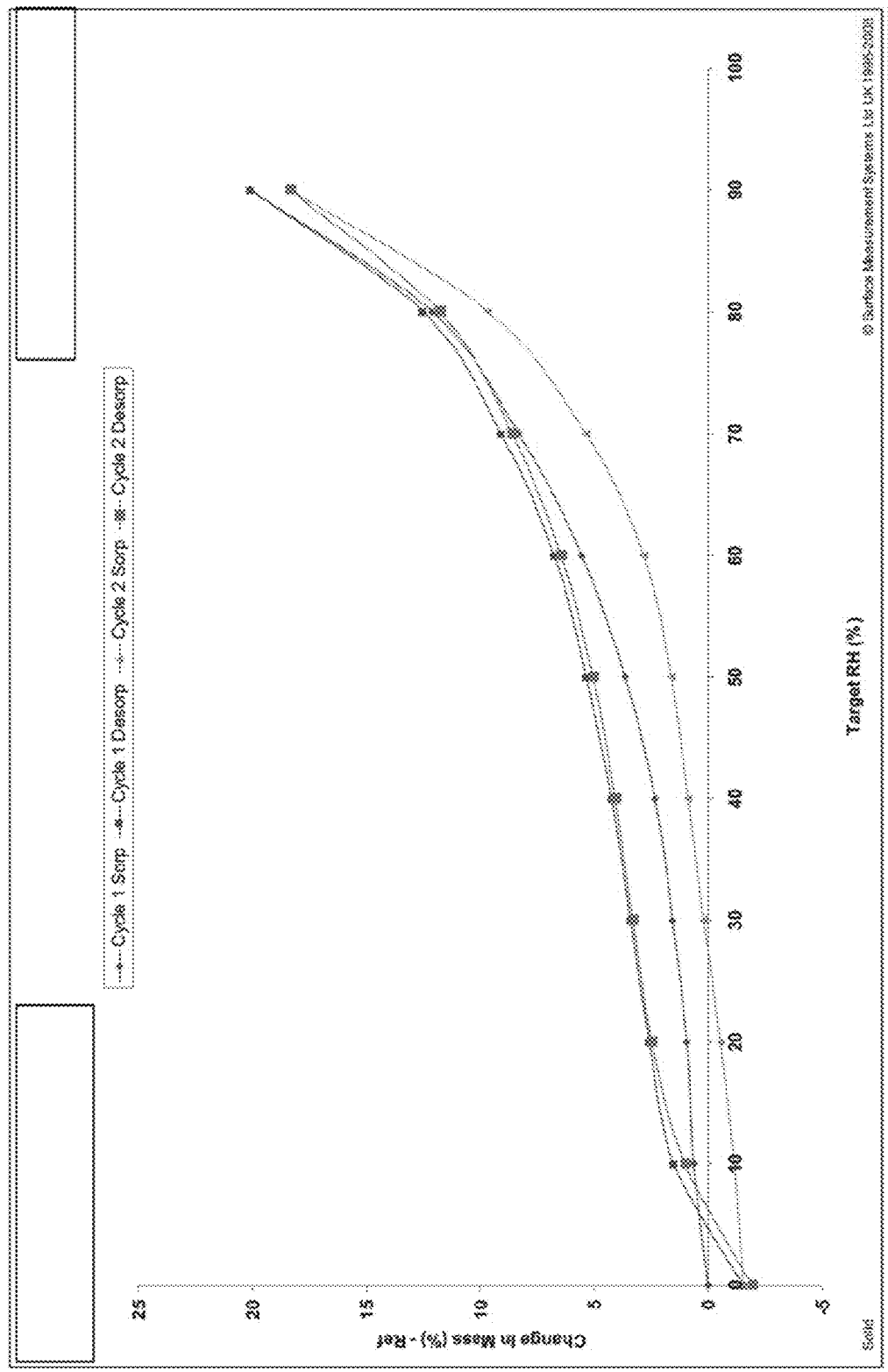

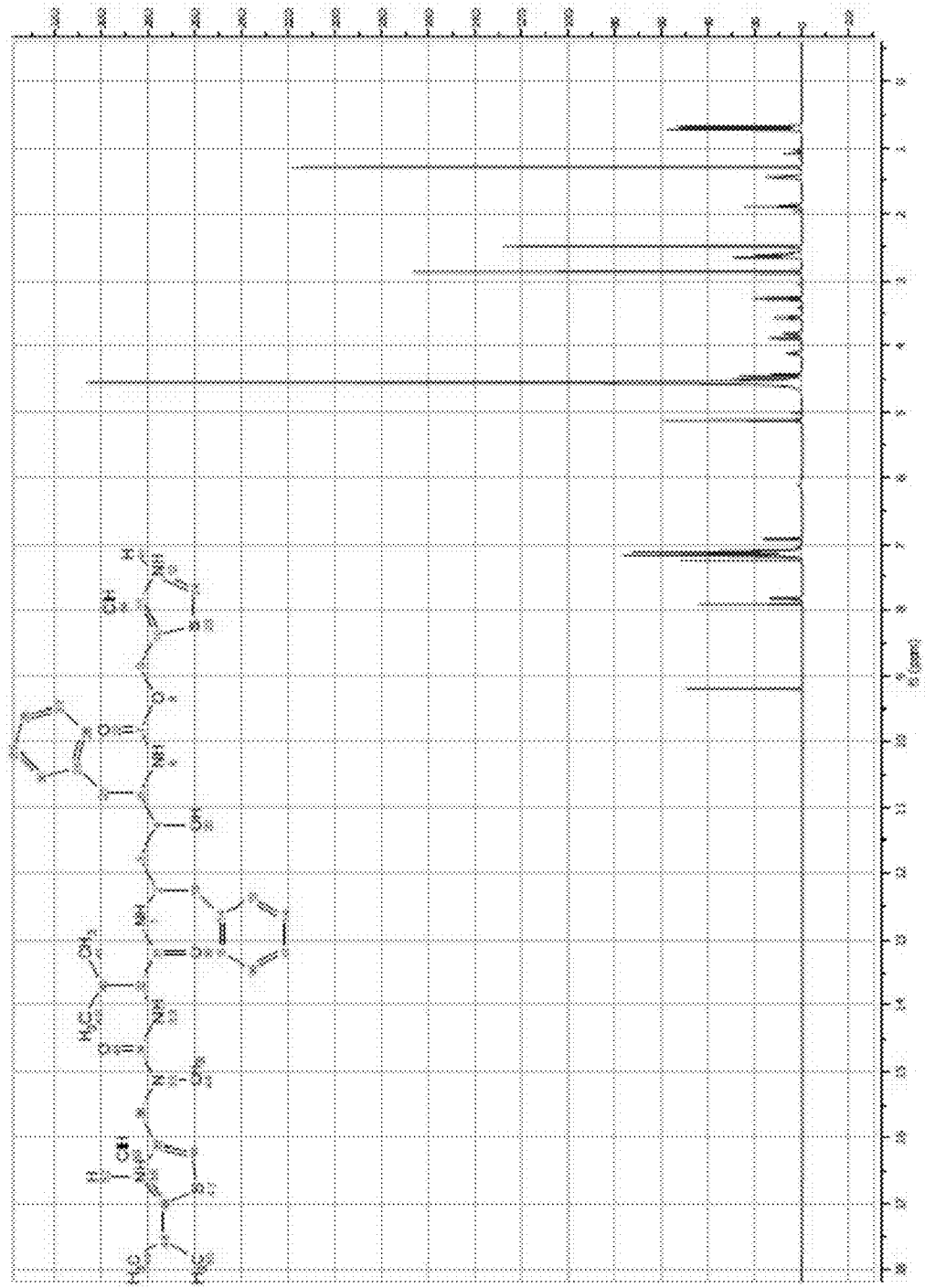
Figure 8: Solution NMR (¹H) of Large-scale Amorphous Ritonavir Bis-Hydrochloride

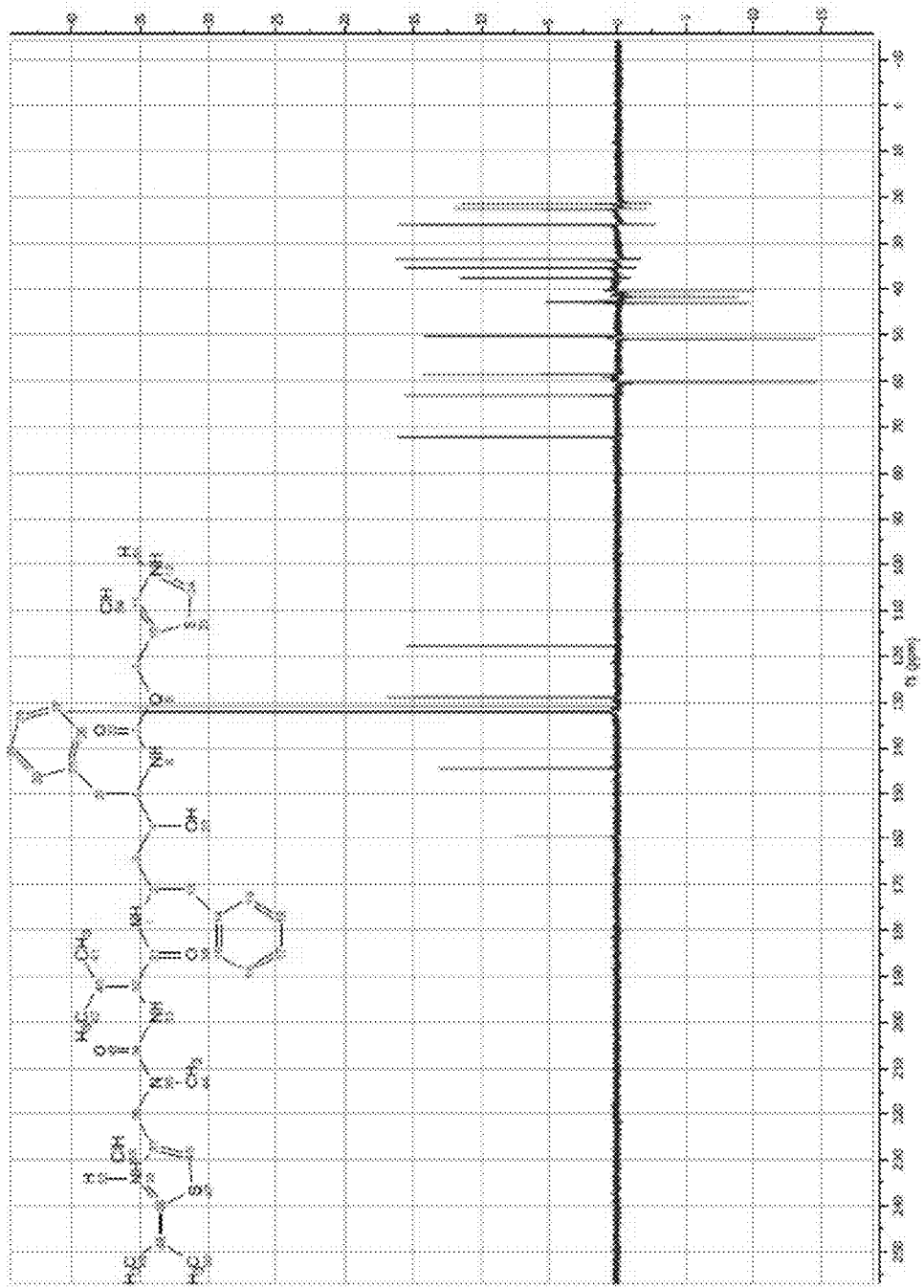

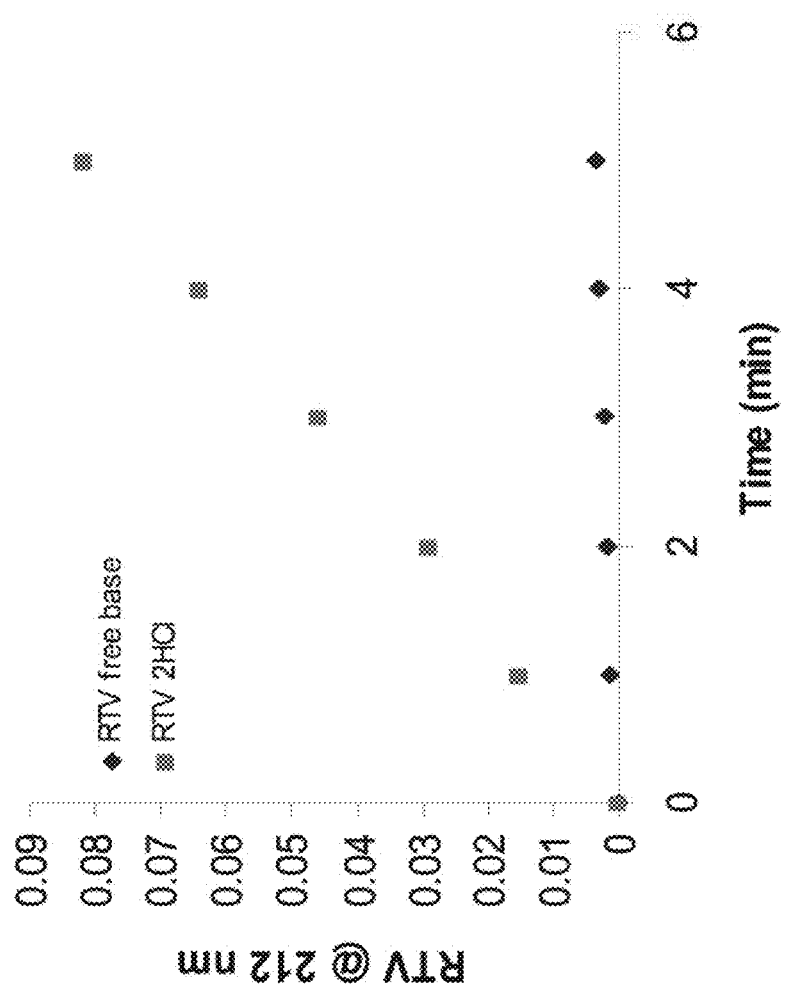

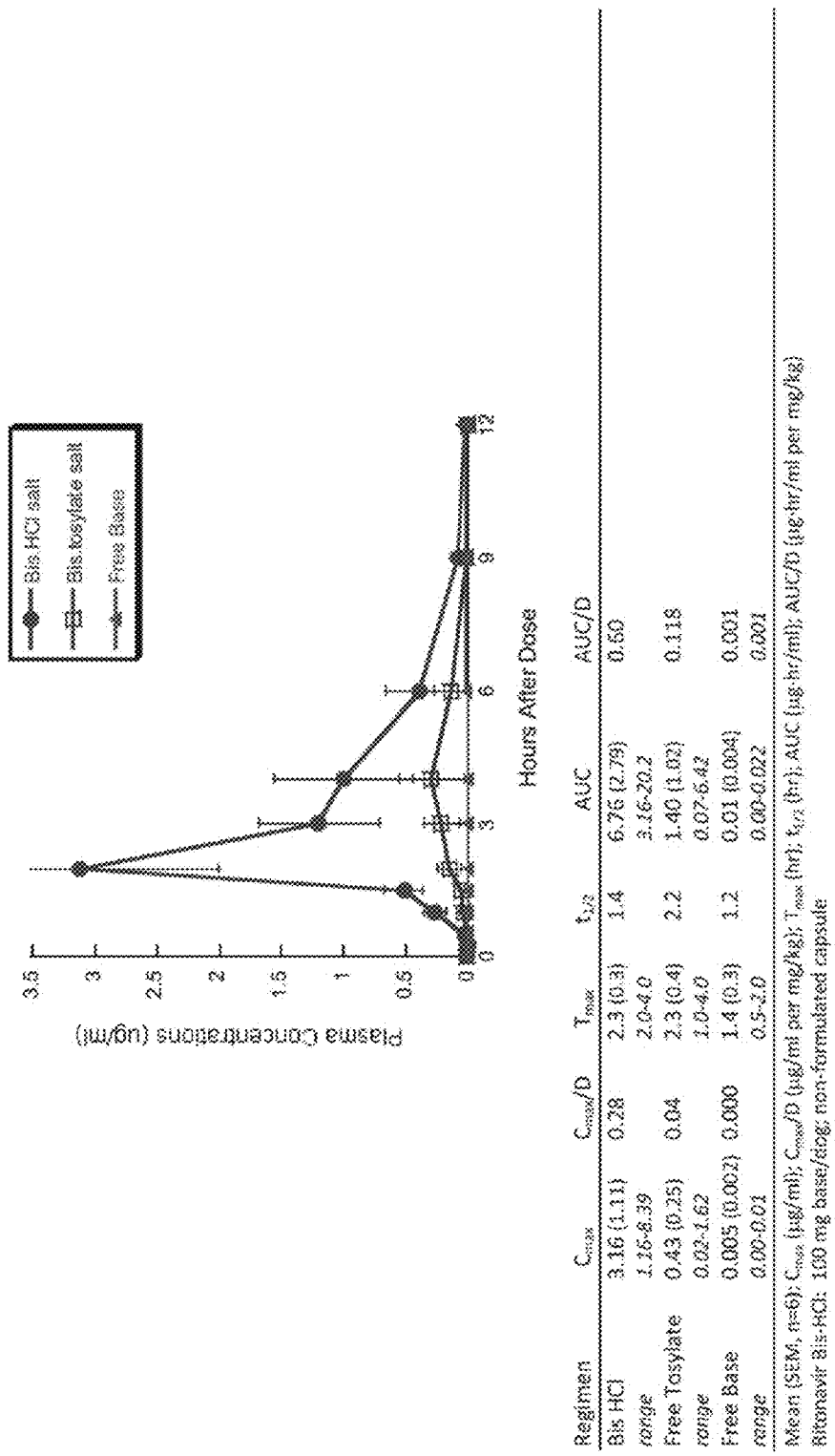

RITONAVIR BIS-HYDROCHLORIDE

FIELD OF THE INVENTION

The invention relates to ritonavir bis-hydrochloride and processes for its preparation, methods for its use as a pharmaceutical agent, and pharmaceutical compositions comprising ritonavir bis-hydrochloride and made from it.

BACKGROUND

Ritonavir, (2S,3S,5S)-5-(N-(N-((N-methyl-N-((2-isopropyl-4-thiazolyl)-methyl)amino)carbonyl)-L-valinyl)amino)-2-(N-((5-thiazolyl)-methoxy-carbonyl)-amino)-1,6-diphenyl-3-hydroxyhexane, has the structure of Formula I:

Formula I

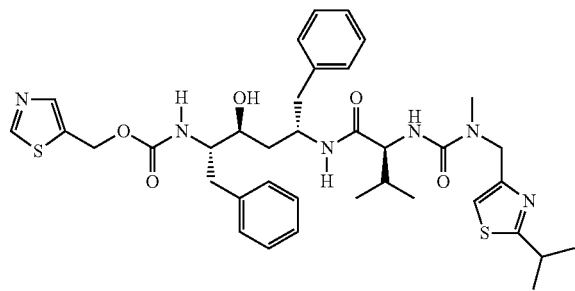

Ritonavir is known to have utility for the inhibition of HIV proteases and the enhancement of the pharmacokinetics of compounds which are metabolized by cytochrome $P_{450}$ 3A4.

SUMMARY OF THE INVENTION

The invention relates to ritonavir bis-hydrochloride, including amorphous ritonavir bis-hydrochloride. In one embodiment, ritonavir bis-hydrochloride of the invention has the structure of Formula II:

Formula II

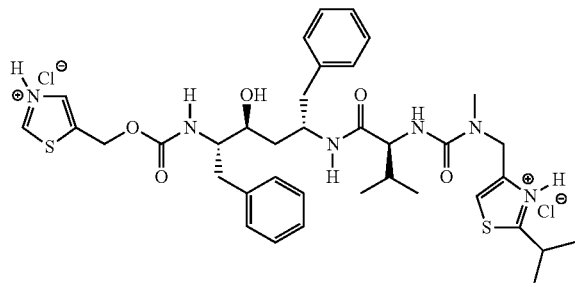

The invention further relates to processes for the preparation of ritonavir bis-hydrochloride, including amorphous ritonavir bis-hydrochloride.

Therapeutic compositions containing the ritonavir bis-hydrochloride represents another embodiment of the invention, as do methods of inhibiting HIV protease or enhancing the pharmacokinetics of compounds which are metabolized by cytochrome $P_{450}$ 3A4 with that ritonavir bis-hydrochloride or therapeutic compositions containing it or made from it.

The present invention is based on an unexpected discovery that ritonavir bis-hydrochloride can be substantially purified or isolated. According to one aspect, the present invention features relatively pure ritonavir bis-hydrochloride. In one embodiment, the relatively pure ritonavir bis-hydrochloride contains less than 50% impurities (e.g., less than 50% other ritonavir salt(s) or form(s)). In another embodiment, the relatively pure ritonavir bis-hydrochloride contains less than 25% impurities (e.g., less than 25% other ritonavir salt(s) or form(s)). In still another embodiment, the relatively pure ritonavir bis-hydrochloride contains less than 10% impurities (e.g., less than 10% other ritonavir salt(s) or form(s)).

According to another aspect, the present invention features substantially pure ritonavir bis-hydrochloride. In one embodiment, the substantially pure ritonavir bis-hydrochloride contains less than 5% other ritonavir salts or forms. In another embodiment, the substantially pure ritonavir bis-hydrochloride contains less than 3% other ritonavir salts or forms. In still another embodiment, the substantially pure ritonavir bis-hydrochloride contains less than 1% other ritonavir salts or forms.

In still another aspect, the present invention features pharmaceutical compositions comprising a therapeutically effective amount of ritonavir bis-hydrochloride. In one embodiment, at least 50% of ritonavir in a pharmaceutical composition of the invention is ritonavir bis-hydrochloride. In another embodiment, at least 60% of ritonavir in a pharmaceutical composition of the invention is ritonavir bis-hydrochloride. In still another embodiment, at least 70% of ritonavir in a pharmaceutical composition of the invention is ritonavir bis-hydrochloride. In yet another embodiment, at least 80% of ritonavir in a pharmaceutical composition of the invention is ritonavir bis-hydrochloride. In another embodiment, at least 90% of ritonavir in a pharmaceutical composition of the invention is ritonavir bis-hydrochloride. In another embodiment, at least 95% of ritonavir in a pharmaceutical composition of the invention is ritonavir bis-hydrochloride. In yet another embodiment, at least 97% of ritonavir in a pharmaceutical composition of the invention is ritonavir bis-hydrochloride. In still another embodiment, at least 99% of ritonavir in a pharmaceutical composition of the invention is ritonavir bis-hydrochloride.

Ritonavir bis-hydrochloride in a pharmaceutical composition of the invention can be, for example and without limitation, in an amorphous form. A pharmaceutical composition of the invention may also contain another drug, such as a drug which is metabolized by cytochrome $P_{450}$ 3A4.

In another aspect, the present invention features processes of making pharmaceutical compositions comprising ritonavir, wherein the processes comprise mixing ritonavir bis-hydrochloride with one or more excipients and, optionally, with one or more other drugs. Preferably, the other drug (s) is metabolized by cytochrome $P_{450}$ 3A4. Ritonavir bis-hydrochloride used in the processes preferably is relatively pure (e.g., at least 50%, 60%, 70%, 80% or 90% pure). More preferably, ritonavir bis-hydrochloride used in the processes is substantially pure (e.g., at least 95%, 97%, or 99% pure).

In yet another aspect, the present invention features processes of making pharmaceutical compositions comprising ritonavir, wherein the processes comprise dissolving ritonavir bis-hydrochloride. In one embodiment, the process comprises dissolving ritonavir bis-hydrochloride in a water-soluble polymer through heating. The melt that contains ritonavir bis-hydrochloride and the water-soluble polymer can be subsequently solidified, which can then be directly tabletted or milled for further processing. In another embodiment, the process comprises dissolving ritonavir bis-hydrochloride in a volatile solvent. The solvent can be subsequently removed (e.g., via spay drying or other evaporation methods) to covert the solution into a powder.

The present invention also features processes for the preparation of ritonavir bis-hydrochloride. The processes comprise dissolving ritonavir (e.g., ritonavir crystalline form I or preferably form II) in an ethyl acetate solution, adding a hydrochloride gas/ethyl acetate solution into the ritonavir/ethyl acetate solution, and then precipitating ritonavir bis-hydrochloride.

In a further aspect, the present invention features methods of treating HIV infection. The methods comprise administering to a patient in need thereof a therapeutically effective amount of ritonavir bis-hydrochloride.

In still another aspect, the present invention features methods of enhancing the pharmacokinetics of a drug that is metabolized by cytochrome $P_{450}$ 3A4. The methods comprise administering to a patient in need of such enhancement an effective amount of ritonavir bis-hydrochloride. The drug can be, for example and without limitation, an HIV protease inhibitor or an HCV protease inhibitor. Preferably, if without co-administration with ritonavir, the drug as used in the methods of the invention would be in an ineffective or inferior amount for treating the intended disease or condition. Thus, by co-administering with ritonavir bis-hydrochloride, the pharmacokinetics (e.g., the blood exposure) of the drug is improved, thereby making the drug effective in treating the intended disease or condition. Ritonavir bis-hydrochloride and the other drug can be, for example, administered simultaneously or sequentially. They can be, for example, co-formulated in a single composition or formulated in separate compositions.

DEFINITIONS

As used herein, the term "substantially pure" means a purity that is greater than about 95 weight percent pure, i.e., it contains less than about five weight percent, such as, for example, between about two and about four weight percent of an impurity or impurities.

As used herein, the term "substantially anhydrous" means that the material is either completely free of water or contains no appreciable amount of water, such as, for example, no more than 5% by weight, and further such as, for example, no more than 1% by weight, based on the weight of the material.

In the following description, various aspects and embodiments of the invention will become evident. Further, these aspects and embodiments are exemplary. Additional objects and advantages of the invention will be set forth in part in the description which follows, and in part will be obvious from the description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following figures, which are described below and which are incorporated in and constitute a part of the specification, illustrate exemplary embodiments according to the invention and are not to be considered limiting of the scope of the invention, for the invention may admit to other equally effective embodiments. The figures are not necessarily to scale, and certain features and certain views of the figures may be shown exaggerated in scale or in schematic in the interest of clarity and conciseness.

FIG. 1 depicts an XRPD pattern from the synthesis of the amorphous ritonavir bis-hydrochloride from Example 1.

FIG. 2 depicts an XRPD pattern from the large-scale synthesis of the amorphous ritonavir bis-hydrochloride from Example 4.

FIG. 3 depicts an infrared spectrum from the large-scale synthesis of the amorphous ritonavir bis-hydrochloride from Example 4.

FIG. 4 depicts an infrared spectrum of amorphous ritonavir free base used in Example 4.

FIG. 5 depicts a DSC trace from the large-scale synthesis of the amorphous ritonavir bis-hydrochloride from Example 4.

FIG. 6 depicts a TGA trace from the large-scale synthesis of the amorphous ritonavir bis-hydrochloride from Example 4.

FIG. 7 depicts a moisture sorption graph from the large-scale synthesis of the amorphous ritonavir bis-hydrochloride from Example 4.

FIG. 8 depicts a solution $^1$H NMR spectrum from the large-scale synthesis of the amorphous ritonavir bis-hydrochloride from Example 4.

FIG. 9 depicts a solution $^{13}$C NMR spectrum from the large-scale synthesis of the amorphous ritonavir bis-hydrochloride from Example 4.

FIG. 10 depicts a graph of the intrinsic dissolution rate of amorphous ritonavir bis-hydrochloride and ritonavir free base.

FIG. 11 depicts a graph of the mean (±SEM) ritonavir plasma concentrations following a 100 mg oral dose in dog (salts vs. free base).

DETAILED DESCRIPTION

Ritonavir Bis-Hydrochloride

Disclosed herein is ritonavir bis-hydrochloride, including the amorphous form of ritonavir bis-hydrochloride.

The methods used to characterize the ritonavir bis-hydrochloride are described below.

The ritonavir bis-hydrochloride, including, for example, the amorphous ritonavir bis-hydrochloride, may possess suitable characteristics for pharmaceutical development. According to one aspect of the invention, the ritonavir bis-hydrochloride of the invention also has been shown to have greater bioavailability than the free base of ritonavir. It is more soluble in water and aqueous solvent systems than the free base of ritonavir itself. In addition, the ritonavir bis-hydrochloride shows better early and late intrinsic kinetic solubility profiles as compared to the free base of ritonavir. Preferably, pharmaceutical compositions comprising an effective amount of amorphous ritonavir bis-hydrochloride are stored under proper dried conditions.

Processes for the Preparation of the Ritonavir Bis-Hydrochloride

The invention relates to processes for making ritonavir bis-hydrochloride, including the amorphous form of ritonavir bis-hydrochloride. In one embodiment, the invention is directed to a process for the preparation of amorphous ritonavir bis-hydrochloride, which includes dissolving ritonavir, for example, substantially pure ritonavir free base, in ethyl acetate (EtOAc), adding an HCl gas/EtOAc solution into the EtOAc/ritonavir solution under conditions sufficient to form amorphous ritonavir bis-hydrochloride as a precipitated product. The precipitated amorphous ritonavir bis-hydrochloride may then be collected by means known in the art, such as filtration, centrifugation, etc.

The exemplary process to make the amorphous ritonavir bis-hydrochloride is shown in the following scheme:

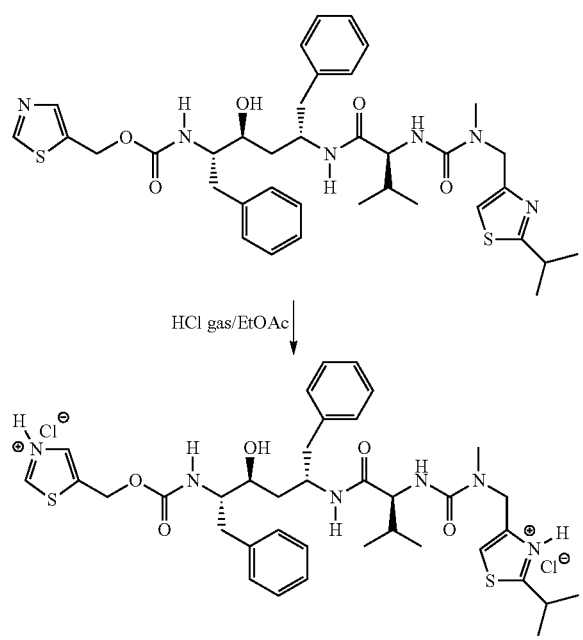 [SMILES: CC(C)c1nc(CN(C)C(=O)N[C@H](C(=O)N[C@@H](Cc2ccccc2)C[C@H](O)[C@H](Cc2ccccc2)NC(=O)OCc2cncs2)C(C)C)cs1 ; CC(C)c1[nH+]c(CN(C)C(=O)N[C@H](C(=O)N[C@@H](Cc2ccccc2)C[C@H](O)[C@H](Cc2ccccc2)NC(=O)OCc2c[nH+]cs2)C(C)C)cs1 ; [Cl-] ; [Cl-]]

Without wishing to be bound by theory, it is believed that the pair of electrons on the nitrogens on the two thiazole groups of ritonavir, shown circled below, reacts with HCl to make the corresponding bis-hydrochloride.

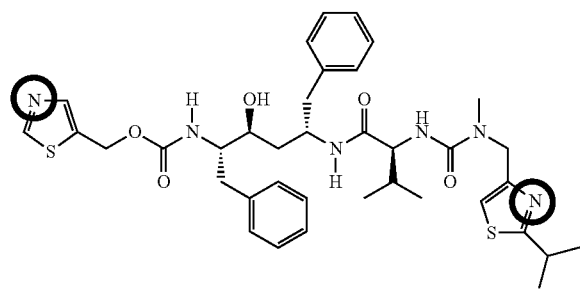

In a first step of the disclosed process, ritonavir, for example, substantially pure ritonavir (e.g., substantially pure ritonavir Form I, or substantially pure ritonavir Form II, or a mixture of ritonavir Form I and Form II), is added to EtOAc, for example, substantially anhydrous EtOAc under inert conditions, such as, for example, under a nitrogen purge, and heated for a time and temperature sufficient to dissolve the ritonavir.

In a second step, once the ritonavir is dissolved in the EtOAc, an HCl gas/EtOAc solution, for example, a substantially anhydrous HCl gas/EtOAc solution, is added into the EtOAc/ritonavir solution under heating and mixing until amorphous ritonavir bis-hydrochloride is formed as a white precipitate. In one embodiment, based on the amount of ritonavir used, about 2 to about 3 molar equivalents of HCl (based on the % w/w of HCl present in the substantially anhydrous HCl gas/EtOAc solution), such as, for example, about 2.1 to about 2.7 molar equivalents of HCl, is added into the EtOAc/ritonavir solution under heating and mixing until a white precipitate is formed.

The HCl gas/EtOAc solution may be made by adding HCl gas, for example, substantially anhydrous HCl gas, into EtOAc, for example, substantially anhydrous EtOAc, under substantially anhydrous conditions and at a temperature from about 0° C. to about 30° C. In one embodiment, the HCl gas/EtOAc solution may contain approximately 5% to 15% w/w HCl. For example, HCl gas may be bubbled into cold, EtOAc under a nitrogen purge.

In one embodiment of the third step, after addition of the HCl gas/EtOAc solution to the EtOAc/ritonavir solution, the resulting white precipitate of amorphous ritonavir bis-hydrochloride is cooled, filtered, washed, and/or dried in the oven under vacuum and inert conditions. For example, the white precipitate is filtered, washed, and dried under vacuum and a nitrogen purge.

Therapeutic Uses of the Ritonavir Bis-Hydrochloride

In another embodiment, the invention relates to therapeutic uses of ritonavir bis-hydrochloride, including, for example, amorphous ritonavir bis-hydrochloride.

The ritonavir bis-hydrochloride according to the invention may be useful as a medicament, which may be used to inhibit HIV protease or enhance the pharmacokinetics of compounds which are metabolized by cytochrome $P_{450}$ 3A4.

Additionally, ritonavir bis-hydrochloride disclosed herein may also be used in a method of treatment of a warm-blooded animal such as, for example, man, by therapy. For example, ritonavir bis-hydrochloride according to the invention may be useful in a method of inhibiting HIV protease or enhancing the pharmacokinetics of compounds which are metabolized by cytochrome $P_{450}$ 3A4.

Moreover, ritonavir bis-hydrochloride according to the invention may be used in the method of treating a human suffering from HIV and/or HCV infections, e.g., by enhancing the pharmacokinetics of drugs that are effective in treating HIV or HCV infection. The use of ritonavir bis-hydrochloride in any of the methods of treating a human described above also form aspects of this invention.

A treatment defined herein may be applied as a sole therapy or may involve combination with one or more other drugs, such as reverse transcriptase inhibitors and/or one or more other HIV and/or HCV protease inhibitors, such as, for example, lopinavir, saquinavir, indinavir, amprenavir, atazanavir, darunavir, fosamprenavir, tipranavir, telaprevir, vaniprevir, nelfinavir, boceprevir, danoprevir, BI 201335, BILN 2061, MK-5172, BMS 650032, TMC435350, GS-9256, IDX-320, elvitegravir, MK-2048, or raltegravir.

Such joint treatment may be achieved by way of the simultaneous, sequential, or separate dosing of the individual components of the treatment. Combination products may be formulated into a single dosage form. In one embodiment, the present invention features a pharmaceutical composition in which ritonavir bis-hydrochloride is co-formulated with at least one drug selected from lopinavir, saquinavir, indinavir, amprenavir, atazanavir, darunavir, fosamprenavir, tipranavir, telaprevir, vaniprevir, nelfinavir, boceprevir, danoprevir, BI 201335, BILN 2061, MK-5172, BMS 650032, TMC435350, GS-9256, IDX-320, elvitegravir, MK-2048, or raltegravir. The co-formulation composition can be a liquid formulation or, preferably, a solid formulation. In another embodiment, the present invention features a pharmaceutical composition which comprises ritonavir bis-hydrochloride and another drug selected from lopinavir, saquinavir, indinavir, amprenavir, atazanavir, darunavir, fosamprenavir, tipranavir, telaprevir, vaniprevir, nelfinavir, boceprevir, danoprevir, BI 201335, BILN 2061, MK-5172, BMS 650032, TMC435350, GS-9256, IDX-320, elvitegravir, MK-2048, or raltegravir. The composition can be a liquid or, preferably, solid composition.

Pharmaceutical Compositions Containing Ritonavir Bis-Hydrochloride

In another embodiment of the invention, the invention also relates to pharmaceutical compositions comprising a therapeutically effective amount of ritonavir bis-hydrochloride according to the invention, including, for example, amorphous ritonavir bis-hydrochloride, and a pharmaceutically acceptable carrier (also known as a pharmaceutically acceptable excipient). As discussed above, ritonavir bis-hydrochloride according to the invention may be, for example, therapeutically useful for inhibiting HIV protease or enhancing the pharmacokinetics of compounds which are metabolized by cytochrome $P_{450}$ 3A4. The effective amounts of ritonavir bis-hydrochloride may differ depending on the intended uses. For example and without limitation, ritonavir bis-hydrochloride may be used at 600 mg BID for the treatment of HIV infection, or 100 mg or less for improving the pharmacokinetics (e.g., blood level or exposure, such as AUC) of other drugs that are metabolized by cytochrome $P_{450}$ 3A4.

Pharmaceutical compositions for inhibiting HIV protease or enhancing the pharmacokinetics of compounds which are metabolized by cytochrome $P_{450}$ 3A4 may contain a therapeutically effective amount of ritonavir bis-hydrochloride according to the present invention. A pharmaceutical composition of the invention may be in any pharmaceutical form which contains the ritonavir bis-hydrochloride according to the invention. The pharmaceutical composition may be, for example, a tablet, capsule, liquid suspension, injectable, topical, or transdermal. The pharmaceutical compositions generally contain, for example, about 1% to about 99% by weight of the ritonavir bis-hydrochloride of the invention and, for example, 99% to 1% by weight of at least one suitable pharmaceutical excipient. In one embodiment, the composition may be between about 5% and about 75% by weight of the ritonavir bis-hydrochloride of the invention with the rest being at least one suitable pharmaceutical excipient or at least one other adjuvant, as discussed below.

A "therapeutically effective amount" of the ritonavir bis-hydrochloride according to the invention can be, without limitation, in the range of about 10-1200 mg daily (oral dose). The actual amount required for treatment of any particular patient may depend upon a variety of factors including, for example, the intended uses (e.g., HIV inhibition vs. pharmacokinetics enhancement), the disease being treated and its severity; the specific pharmaceutical composition employed; the age, body weight, general health, sex, and diet of the patient; the mode of administration; the time of administration; the route of administration; and the rate of excretion of the ritonavir bis-hydrochloride; the duration of the treatment; any drugs used in combination or coincidental with the specific compound employed; and other such factors well known in the medical arts. These factors are discussed in Goodman and Gilman's "The Pharmacological Basis of Therapeutics," Tenth Edition, A. Gilman, J. Hardman and L. Limbird, eds., McGraw-Hill Press, 155-173 (2001), which is incorporated herein by reference. The ritonavir bis-hydrochloride according to the invention and pharmaceutical compositions containing it may be used in combination with antiretroviral or other agents that are generally administered to a patient being treated for HIV or AIDS and HCV. They may also be co-formulated with one or more of such agents in a single pharmaceutical composition.

Depending on the type of pharmaceutical composition, the pharmaceutically acceptable carrier may be chosen from any one or a combination of carriers known in the art. The choice of the pharmaceutically acceptable carrier depends upon the pharmaceutical form and the desired method of administration to be used. Preferred carriers include those that do not substantially alter the salt of ritonavir or produce undesirable biological effects or otherwise interact in a deleterious manner with any other component(s) of the pharmaceutical composition.

The pharmaceutical compositions of the invention may be prepared by methods know in the pharmaceutical formulation art, for example, see Remington's Pharmaceutical Sciences, 18th Ed., (Mack Publishing Company, Easton, Pa., 1990), which is incorporated herein by reference. In a solid dosage form, the ritonavir bis-hydrochloride may be admixed with at least one pharmaceutically acceptable excipient such as, for example, sodium citrate or dicalcium phosphate or (a) fillers or extenders, such as, for example, starches, lactose, sucrose, glucose, mannitol, and silicic acid, (b) binders, such as, for example, cellulose derivatives, starch, alignates, gelatin, polyvinylpyrrolidone, sucrose, and gum acacia, (c) humectants, such as, for example, glycerol, (d) disintegrating agents, such as, for example, agar-agar, calcium carbonate, potato or tapioca starch, alginic acid, croscarmellose sodium, complex silicates, and sodium carbonate, (e) solution retarders, such as, for example, paraffin, (f) absorption accelerators, such as, for example, quaternary ammonium compounds, (g) wetting agents, such as, for example, cetyl alcohol, and glycerol monostearate, magnesium stearate and the like (h) adsorbents, such as, for example, kaolin and bentonite, and (i) lubricants, such as, for example, talc, calcium stearate, magnesium stearate, solid polyethylene glycols, sodium lauryl sulfate, or mixtures thereof. In the case of capsules, tablets, and pills, the dosage forms may also comprise buffering agents.

Pharmaceutically acceptable adjuvants known in the pharmaceutical formulation art may also be used in the pharmaceutical compositions of the invention. These include, but are not limited to, preserving, wetting, suspending, sweetening, flavoring, perfuming, emulsifying, and dispensing agents. Prevention of the action of microorganisms may be ensured by inclusion of various antibacterial and antifungal agents, for example, parabens, chlorobutanol, phenol, sorbic acid, and the like. It may also be desirable to include isotonic agents, for example, sugars, sodium chloride, and the like. If desired, a pharmaceutical composition of the invention may also contain minor amounts of auxiliary substances such as wetting or emulsifying agents, pH buffering agents, antioxidants, and the like, such as, for example, citric acid, sorbitan monolaurate, triethanolamine oleate, butylated hydroxytoluene, etc.

Solid dosage forms as described above may be prepared with coatings and shells, such as enteric coatings and others well known in the art. They may contain pacifying agents, and can also be of such composition that they release the active compound or compounds in a certain part of the intestinal tract in a delayed manner. Non-limiting examples of embedded compositions that may be used are polymeric substances and waxes. The active compounds may also be in microencapsulated form, if appropriate, with one or more of the above-mentioned excipients.

Suspensions, in addition to the active compounds, may contain suspending agents, such as, for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Because the amorphous form is maintained during preparation, solid dosage forms are preferred for the pharmaceutical composition of the invention. Solid dosage forms for oral administration, which includes capsules, tablets, pills, powders, and granules, may be used. In such solid dosage forms, the active compound may be mixed with at least one inert, pharmaceutically acceptable excipient (also known as a pharmaceutically acceptable carrier). Ritonavir bis-hydrochloride according to the invention may also be used as precursors in the formulation of liquid pharmaceutical compositions. Administration of the ritonavir bis-hydrochloride in pure form or in an appropriate pharmaceutical composition may be carried out via any of the accepted modes of administration or agents for serving similar utilities. Thus, administration may be, for example, orally, buccally, nasally, parenterally (intravenous, intramuscular, or subcutaneous), topically, transdermally, intravaginally, intravesically, or intrasystemically, in the form of solid, semi-solid, lyophilized powder, or liquid dosage forms, such as, for example, tablets, suppositories, pills, soft elastic and hard gelatin capsules, powders, solutions, suspensions, or aerosols, or the like, such as, for example, in unit dosage forms suitable for simple administration of precise dosages. One route of administration may be oral administration, using a convenient daily dosage regimen that can be adjusted according to the degree of severity of the disease-state to be treated.

The invention also relates to preparation of a medicament using the ritonavir bis-hydrochloride for inhibiting HIV protease or enhancing the pharmacokinetics of compounds which are metabolized by cytochrome $P_{450}$ 3A4.

Pharmaceutical Compositions Containing Ritonavir Prepared from Ritonavir Bis-Hydrochloride The invention also relates to pharmaceutical compositions comprising a therapeutically effective amount of ritonavir prepared by melting ritonavir bis-hydrochloride according to the invention and at least one excipient to produce a melt and solidifying the melt. In another embodiment, pharmaceutical compositions comprising a therapeutically effective amount of ritonavir may be prepared by dissolving ritonavir bis-hydrochloride according to the invention and at least one excipient in a solvent, and drying the solvent. In another embodiment, pharmaceutical compositions comprising a therapeutically effective amount of ritonavir may be prepared by milling ritonavir bis-hydrochloride according to the invention and at least one excipient. In another embodiment, pharmaceutical compositions comprising a therapeutically effective amount of ritonavir may be prepared by dissolving ritonavir bis-hydrochloride according to the invention in a solution.

Any form of ritonavir bis-hydrochloride according to the invention may be used to prepare a pharmaceutical composition comprising a therapeutically effective amount of ritonavir. These pharmaceutical compositions are also therapeutically useful for inhibiting HIV protease or enhancing the pharmacokinetics of compounds which are metabolized by cytochrome $P_{450}$ 3A4.

EXAMPLES

The following analytical techniques were used in the examples below:

High Performance Liquid Chromatography (HPLC):

HPLC studies were performed on a high performance liquid chromatograph capability, auto sampler, variable temperature column oven, and variable wavelength UV detector, and in-line degas system. The electronic integrator or data acquisition system is a YMC Butyl C4 column, 15 cm×4.6 mm, 3 µm, part number BU12503-1546WT or equivalent Mobile phase filtering Unit.

Potassium phosphate monobasic solution (0.03 M) Preparation: Potassium phosphate monobasic solution (0.03 M) was prepared by dissolving about 8.2 g of $KH_2PO_4$ (Fischer Scientific) in 2.0 L Milli-Q® water. The solution was mixed for 10 minutes at room temperature and then filtered through a 0.45 µm nylon membrane. 2 L of filtered solution was stored in the fume hood.

Diluent Preparation: 500 mL of the $KH_2PO_4$ 0.03 M solution and 500 mL acetonitrile (Rathburn HPLC Grade S) were mixed and filtered through a 0.45 µm nylon membrane.

Mobile Phase A Preparation: 1380 mL of the $KH_2PO_4$ 0.03 M solution, 360 mL of the acetonitrile, 160 mL of THF (Sigma Aldrich), and 100 mL of N-butanol (Sigma Aldrich) were mixed.

Mobile Phase B Preparation: 400 mL of the $KH_2PO_4$ 0.03 M solution, 470 mL of the acetonitrile, 80 mL of the THF, and 50 mL of the N-butanol were mixed.

Sample Preparation: Ritonavir pure weight=47.33 mg diluted with 50 mL of diluent. Ritonavir bis-hydrochloride EtOAc weight=50.57 mg diluted with 50 mL of diluent.

Typical Chromatographic Conditions
Injection Volume=50 µL
Flow Rate=1.0 mL/min
Detector Wavelength=240 nm
Column Temperature=60° C.
Syringe Flush=3/1 of acetonitrile/water (if necessary)
Data Collection=40 min for Impurity Working Standard, Assay Standard, and Assay Sample Preparation; 155 min for Impurity Sample Preparation
Range=1.0 AUFS and suitable setting on the electronic integrator Polarized Light Microscopy (PLM):

Solids were examined by polarized light microscopy to determine the presence or absence of birefringence. Microscopic visual examination was performed using a polarizing microscope (Olympus Model BX51, Olympus Optical Co. Ltd., Tokyo, Japan) equipped with a color video camera (Qimaging MicroPublisher 5.0 RN Camera, Qimaging Co., Surrey, Canada). Images were captured and analyzed using Clemex $PS^3$ image analysis software (version 4.1 Clemex Technologies inc., Longueuil, Canada).

Solution Nuclear Magnetic Resonance (NMR) ($^1H$ and $^{13}C$):

NMR data were collected on a Varian Mercury NMR Spectrometer (Varian Inc, Palo Alto, USA) operating at 400 MHz $^1H$ frequency. This instrument is controlled by a Sun Ultra 10 workstation running solaris 5.8 and spectrometer software VNMR 6.1 C. Typical acquisition parameters are: 32-128 scans of 32 K complex points; a sweep width of −2 to 20 ppm; acquisition time of 3.5 sec with a relaxation delay of 1 sec using a 45° pulse width. Probe temperature is set to 25° C. Spectra are referenced to internal TMS or the residual protonated solvent resonance.

X-Ray Powder Diffraction (XRPD):

XRPD data were collected using a G3000 diffractometer (Inel Corp., Artenay, France) equipped with a curved position sensitive detector and parallel beam optics. The diffractometer was operated with a copper anode tube (1.5 kW fine focus) at 40 kV and 30 mA. An incident beam germanium monochromator provided monochromatic $K\alpha 1$ radiation. The diffractometer was calibrated using the attenuated direct beam at one-degree intervals. Calibration was checked using a silicon powder line position reference standard (NIST 640c). The instrument was computer controlled using the Symphonix software (Inel Corp., Artenay, France) and the data was analyzed using the Jade software (version 6.5, Materials Data, Inc., Livermore, Calif.). The sample was loaded onto an aluminum sample holder and leveled with a glass slide.

Fourier Transform Infrared Spectroscopy (IR):

An ASD LabSpec 5000 Portable Near Infrared Instrument equipped with IndicoPro v5.5 software was used to determine the IR peaks.

Differential Scanning calorimetry (DSC):

A DSC (0-2000, TA Instruments, New Castle, Del.) equipped with Universal Analysis 2000 software (Version 4.5A, TA Instruments, New Castle, Del.) was used to determine the DSC thermal traces. The temperature axis was calibrated with biphenyl, indium, and tin standards. The cell constant was calibrated with indium. Unless otherwise stated, the sample (2-5 mg) was encapsulated in a ventilated aluminum pan, and heated at a rate of 10° C./min under a nitrogen gas flow of 50 mL/min during the study.

Thermogravimetric Analysis (TGA):

TGA traces were collected on a thermal balance (Q-500, TA Instruments, New Castle, Del.) equipped with a data analyzer (Universal Analysis 2000, version 4.5A, TA Instruments, New Castle, Del.). During experiments, the furnace was purged with nitrogen at 60 mL/min, while the balance chamber was purged at 40 mL/min. Temperature of the TGA furnace was calibrated using curie points of alumel and nickel. Sample size ranged from 2 to 20 mg, and a heating rate of 10° C./min was used.

TGA/Mass Spectrometry (TGA/MS):

Thermogravimetric analysis data was collected with a TGA Q-5000 (TA Instruments, New Castle, Del.) equipped with an integral Q5000 SA autosampler. The instrument was operated and data was evaluated with Thermal Advantage Release 4.6.6 for Q-series version 2.6.0.362 operating software. The temperature axis was calibrated with indium and aluminum standards. The samples were loaded in aluminum open pans and scanned at 10° C./min. A 50 mL/min nitrogen purge to the sample chamber was used. The mass of evolved gas is analyzed with PFEIFFER GSD 301 T3 ThermoStar (PFEIFFER Vacuum, Asslar, Germany). The instrument is operated and data evaluated with Software Quadstar 32-bit (V7.01, Inficon, LI-9496 Balzers, Liechtenstein).

Dynamic Moisture Sorption Balance:

Hygroscopicity was evaluated on a dynamic moisture sorption balance (IGAsorp, Hiden Isochema, Warrington, UK) equipped with a data analyzer (IGAsorp, version 6.0.0.23, Hiden Isochema, Warrington UK). The balance was calibrated using standardized weights of 20, 50, and 100 mg. The RH probe was calibrated using standardized salt solutions of Lithium Chloride, Potassium Carbonate, and Sodium Chloride. During the experiment, the flow rate of nitrogen gas at different relative humidity was 250 mL/min. For anhydrous materials, the sample was first dried with dry nitrogen at 50° C. for two hours. The temperature was then set to 25° C. and the relative humidity was changed from 0% to 90% and back to 0% at 10% interval. For hydrated samples, the temperature was set to 25° C. and the relative humidity was changed at 10% interval from 30% to 90%, back to 10%, and then to 90%.

Intrinsic Dissolution Rate (IDR):

Amorphous ritonavir bis-hydrochloride and ritonavir free base were compressed in a stationary disc (compression force: 1,500 lbs for 1 min; Tablet diameter: 9 mm). Drug dissolution was measured using in USP II (Dissolution medium: 200 mL pH 6.8 phosphate buffer; Paddle speed: 100 rpm).

PREPARATIVE EXAMPLES

Example 1

Preparation of Amorphous Ritonavir Bis-Hydrochloride 1.1 Preparation of Hydrochloride Gas/EtOAc Solution:

180 g of EtOAc anhydrous (Aldrich, 99.8%) was cooled to 15° C., and transferred into a conical flask. The system was purged with nitrogen. Ca. 21.14 g of hydrochloride gas was then bubbled slowly (for example, by microbubbles for dissolution) into the cold EtOAc under agitation. The dissolution was carried out under nitrogen. The unsolubilized, excess hydrochloride was quenched with a NaOH aqueous solution. The dissolution was slightly exothermic. The EtOAc solution may need to be cooled down several times. The temperature was kept below 30° C. The weight of the conical flash and EtOAc was measured before and after the addition.

The following calculation was used to determine the concentration of hydrochloride per gram of solution:

180 g of EtOAc+21.14 g of HCl=201.14 g.

Therefore, 21.14/201.14=0.1051 g of HCl/g of solution, i.e., ca. 10.51% w/w HCl.

1.2 Calculation of Volume of HCl Gas/EtOAc Solution to be Added 20 g of ritonavir, which has a molecular weight of 720.94 g/mol, was used to make the amorphous ritonavir bis-hydrochloride (i.e., ca. 27.74 mmol). Ca. 2.1 equivalents of HCl is necessary for every one molecule of ritonavir (i.e., to quench the two basic nitrogen in the aromatic rings of ritonavir and to complete the reaction). Therefore, the quantity of HCl/EtOAc solution needed=[(20/720.94)×2.1×36.45 (HCl molecular weight))×(201.14/21.14)=20.2 g. Up to 2.5 equivalents of HCl can be added without any impact on the quality of the product.

1.3 Preparation of Amorphous Ritonavir Bis-Hydrochloride 20.0 g of ritonavir was added to 1 L of anhydrous EtOAc (Aldrich, 99.8%) in a 2 L three-neck jacketed flask reactor under a nitrogen atmosphere. The reaction mixture was stirred and warmed up to about 65° C. until complete dissolution. Once the ritonavir was completely dissolved, the solution was cooled down to about 30° C. 20.2 g (i.e., ca. 2.12 g or 58.24 mmol of HCl) of the HCl/EtOAc solution prepared in 1.2 above was added dropwise to the ritonavir solution over about 30 minutes. The first acidic drop gave a white solid, which was solubilized just after appearing. After a few drops, a cloudy solution appeared. After the addition ended, the amorphous ritonavir bis-hydrochloride was obtained as a white slurry. No exotherm was observed during the addition. The reaction mixture was mixed for another 30-60 minutes at 20 to 35° C. An aliquot was taken (2 mL) and transferred to a small vial. Waited for 15 minutes for decantation. A colorless liquid appeared on the top. A few additional quantity of the HCl/EtOAc solution were added without agitation. When there is no more additional precipitation, the reaction was complete.

The slurry was cooled down to 20° C., and then transferred to a Buchner funnel for a quick filtration under vacuum. The filter cake was kept under nitrogen during the filtration. The hydrochloride was hygroscopic. Once no more liquid was removed, the white cake was washed with 100 mL of EtOAc. The filtration was continued under vacuum and a nitrogen blanket. Once no more liquid was removed, the vacuum was stopped and the cake was left under nitrogen stream overnight at room temperature.

The following day, the solid product was ground to a powder and then dried in a vacuum at 40° C. for 24 hours.

KF using a 701 KF Titrino on the dried product showed about 1.8% to 2.5% water, which was probably introduced during the overnight nitrogen purge.

The amorphous ritonavir bis-hydrochloride was analyzed by the HPLC method described above. The assay was generally 99.5% and the yield was 95-105% at this stage.

1.4 XRPD Characterization of Amorphous Ritonavir Bis-Hydrochloride

FIG. 1 shows the XRPD pattern of amorphous ritonavir bis-hydrochloride acquired at room temperature (about 25° C.). The spectra is characterized by a broad peak and the absence of sharp peaks, which is consistent with an amorphous material.

1.5 Polarized Light Microscopy of Amorphous Ritonavir Bis-Hydrochloride

The amorphous ritonavir bis-hydrochloride was examined using PLM. No ritonavir bis-hydrochloride particles with birefringence were observed for the amorphous ritonavir bis-hydrochloride at 100× magnification. At 200× and 500× magnification, the majority of ritonavir bis-hydrochloride particles were amorphous, but a few particles were found to have birefringence.

Example 2

Alternative Preparation of Amorphous Ritonavir Bis-Hydrochloride 2.1 Preparation of Amorphous Ritonavir Bis-Hydrochloride:

Ritonavir, in an amount of 2 g (i.e., ca. 2.77 mmol), was dissolved in 50 mL of EtOAc solution in a hot water bath under an inert atmosphere. The reaction mixture was stirred for ca. 20 to 60 minutes at 60° C.±10° C. An HCl gas/EtOAc solution was formed by bubbling 1.4 g of HCl gas into 16.6 g of cold EtOAc to make an 18 g HCl gas/EtOAc solution containing 1.4 g HCl, i.e., ca. 7.78% w/w HCl. Once the ritonavir was completely dissolved, 2.67 g of the HCl gas/EtOAc (i.e., ca. 0.21 g or 5.76 mmol of HCl) was added dropwise over ca. 2 minutes to dissolved ritonavir while still hot. Under strong mixing, a white precipitate formed. Therefore, ca. 2.1 equivalents of HCl were used for every one molecule of ritonavir.

The white precipitate slurry was mixed at room temperature for 5 minutes and then stored in a refrigerator for overnight at 0°±5° C. The slurry was then filtered and washed under vacuum using 30 mL of EtOAc for about 30 sec. The solid was stored under vacuum in a desiccator (with $CaCl_2$ powder) for 72 hours, ca. 2.11 g of the solid, white product was obtained. The process has been shown to provide a yield of an amorphous ritonavir bis-hydrochloride of 92 to 100 percent with a chromatographic purity of 95 to 100 percent.

2.2 HPLC of Amorphous Ritonavir Bis-Hydrochloride

The amorphous ritonavir bis-hydrochloride product was analyzed by the HPLC method described above in order to verify the quality of the salt and observe whether there was any degradation. It was determined that no degradation occurred (assay 99.6%).

2.3 HCl Salt Analysis of Amorphous Ritonavir Bis-Hydrochloride

A titration analysis of the amorphous ritonavir bis-hydrochloride by NaOH aq (C=0.1 N) with a few drops of 10% phenol phtaleine in EtOH showed the presence of 2HCl molecules for 1 molecule of ritonavir.

Example 3

Second Alternative Preparation of Amorphous Ritonavir Bis-Hydrochloride

Amorphous ritonavir bis-hydrochloride was prepared using aqueous media. 100 mL (i.e., 78.6 g) of isopropanol was first transferred into a conical flask. 2.49 g of HCl aqueous solution (32% conc., 2.19 eq) were dissolved in the isopropanol (IPA) and the resulting solution was well mixed. In another conical flask, 7.20 g of ritonavir (i.e., 10 mmol), were dissolved in 200 mL of IPA (i.e., 157.1 g). The solution was mixed until complete dissolution at 40-45° C. Once complete ritonavir dissolution was obtained, HCl/IPA solution was added dropwise over 10 minutes to the ritonavir dissolved in the IPA. The reaction was cooled down to room temperature and was left under mixing for 4 hours. The reaction mixture was evaporated to dryness under vacuum at 35-40° C. The residue was taken back in 140 mL of IPA (i.e., 110.0 g). The solvent was distilled in vacuum at 35-40° C. until dryness. The residue was taken back in 80 mL of IPA (i.e., 62.8 g) and the solvent was distilled again in vacuum at 35-40° C. until dryness in order to remove all the residual water. The residue was taken back in 80 mL of IPA (i.e., 62.8 g) and warmed up for a complete dissolution. This ritonavir bis-hydrochloride solution was added slowly over 1 hour at room temperature in 400 mL of heptane. The white precipitate obtained was then filtrated and washed with 100 mL of heptane and the dried in a desiccator under vacuum. 7.3 g of product was obtained, which results in a yield of ca. 92.1%, assay 99.6%.

Example 4

Large-Scale Preparation of Amorphous Ritonavir Bis-Hydrochloride 4.1 Preparation of Amorphous Ritonavir Bis-Hydrochloride:

A large-scale preparation of amorphous ritonavir bis-hydrochloride was performed. To prepare the HCl gas/EtOAc solution, 100 mL (i.e., 89.6 g) of EtOAc is first transferred into a conical flask. 8.40 g of HCl gas was purged and dissolved in the EtOAc for over 30 minutes at 0 to 30° C. to make a 98 g HCl gas/EtOAc solution containing 8.40 g HCl, i.e., 8.57% w/w HCl.

20 g of ritonavir (i.e., 20.74 mmol) were to be used to prepare the amorphous ritonavir bis-hydrochloride. In order to add 2.1 equivalents of the HCl gas/EtOAc solution for every molecule of ritonavir, 24.78 g (ca. 2.1 eqs. of HCl) of the HCl gas/EtOAc solution was added. The 20 g of ritonavir was dissolved in 350 mL of EtOAc by first warming the solution up to 60° C.±10° C. for 20 to 60 minutes and then cooling the solution down to 20 to 40° C. for 30 to 120 minutes. Once the temperature was correct, 24.78 g of the HCl gas/EtOAc solution was added dropwise over 10 minutes to the ritonavir dissolved in the EtOAc to make a white precipitate. The reaction mixture was mixed for another 10 minutes at 38° C. and then 1 hour at 15° C. The white precipitate was then filtrated and washed with 150 mL of EtOAc and the dried in a desiccator. After one wash inside the reactor, some crust of the white product was left on the walls, which lowered the yield.

The product was left in the desiccator for ca. 48 hours. Afterwards, 20.2 g of the product was obtained from the desiccator, ground, and then dried for an additional 40° C. for 48 hours under vacuum.

20.2 g of the amorphous ritonavir bis-hydrochloride results in a yield of ca. 91.8%, which was lowered, at least in part, by the product left on the walls of the reactor.

The 20.2 g of product was dried in a vacuum oven at 40° C. for 40 hours. Afterwards, 21.6 g of the product was obtained, which results in a yield of ca. 106.9%.

4.2 KF of Amorphous Ritonavir Bis-Hydrochloride:

The large-scale amorphous ritonavir bis-hydrochloride had an experimental KF of 3.1%.

4.3 XRPD Characterization of Amorphous Ritonavir Bis-Hydrochloride

FIG. 2 shows the XRPD pattern of large-scale amorphous ritonavir bis-hydrochloride acquired at room temperature (about 25° C.). The spectra are characterized by a broad peak and the absence of sharp peaks, which is consistent with an amorphous material.

4.4 Infrared Characterization of Amorphous Ritonavir Bis-Hydrochloride Vs. Ritonavir FIGS. 3 and 4 show the infrared pattern of the large-scale amorphous ritonavir bis-hydrochloride and amorphous ritonavir free base starting material acquired at room temperature (about 25° C.), respectively. The thiazole group contains an imine type functionality within the heteroaromatic ring structure. The appearance of absorption bands at 2541, 1961, and 1896 cm$^{-1}$ in the mid-infrared (MIR) spectrum on ritonavir bis-hydrochloride are indicative of imine hydrohalide type functional group stretching vibrations. The two bands at 1961 and 1896 cm$^{-1}$ distinguish imine hydrohalides from amine hydrohalides. The FT-MIR of ritonavir bis-hydrochloride is consistent with the proposed structure's chemical functionality. The following Tables 1 and 2 provide a comparison of representative peaks of the large-scale amorphous ritonavir bis-hydrochloride and the amorphous ritonavir free base starting material, respectively.

TABLE 1

Infrared Peaks for Amorphous Ritonavir Bis-Hydrochloride[a]

| Observed MIR Absorption Band/ Range (cm$^{-1}$) at 4 cm$^{-1}$ resolution** | Assigned Functional Group(s) from the MIR Spectrum | Ref.* Page |
|---|---|---|
| 3262** | 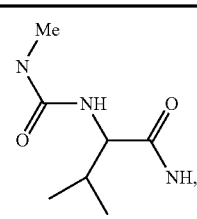 $\nu_a$ OH, N—H | 94, 108, 143[1] |
| 3059, 3026** | 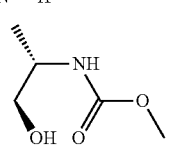 $\nu$ (═CH ring), $\nu$ —C—H | 158[1], 301[2] |
| 2964, 2933, 2872** | $\nu_a$ and $\nu_s$, CH$_3$, —CH$_2$ | 50[1] |
| 2541, 1961, 1896 |  $\nu$ | 109, 113[1] |
| 1710 | $\nu$ Amide I, C═O | 153[1] |
| 1641** | 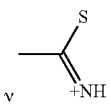 $\nu$ Amide II, C═O, $\nu$ (—C═C— ring) | 154, 160[1] |
| 1526 | 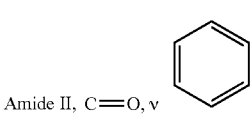 $\nu$ —C═N, $\nu$ —C═C— | 216[3] |
| 1454** | $\nu_a$ CH$_3$, Y$_b$ C—N—H | 52[1], 144[2] |

TABLE 1-continued

Infrared Peaks for Amorphous Ritonavir Bis-Hydrochloride[a]

| Observed MIR Absorption Band/ Range (cm$^{-1}$) at 4 cm$^{-1}$ resolution** | Assigned Functional Group(s) from the MIR Spectrum | Ref.* Page |
|---|---|---|
| 1387** | $\delta$—C(CH$_3$)$_2$, $\nu_{ip}$ —C=N, $\nu$ —C—S—C (thiazole), $\nu$ —C=C— (phenyl ring), (thiazole) | 52, 60[1], 303[2], 216[3] |
| 1293** | $\delta$ —CH$_2$, —CH, $\gamma_\omega$ —CH$_2$, —CH | 51, 227[4] |
| 1251** | $\nu$ —C—N, C—O (coupled), $\delta$ (phenyl) (—C—H ring), $\nu$ —C—O—C | 101, 154, 159[1] |
| 1175, 1129, 1081, 1047** | $\gamma_{bip}$ C—H (phenyl ring), $\nu$ C-X (S) (thiazole), $\nu_a$ C—O—C, $\nu$ —C—O | 154, 159[1], 216[3], 303[2] |
| 960, 938, 876, 859, 754, 702** | $\delta_{op}$ (phenyl ring), $\delta$ (phenyl ring C—H), $\nu$ C-X (S) (thiazole) | 160, 162, 163, 207[1] |

TABLE 2

Infrared Peaks for Amorphous Ritonavir Free Base[a]

| Observed MIR Absorption Band/ Range (cm$^{-1}$) at 4 cm$^{-1}$ resolution** | Assigned Functional Group(s) from the MIR Spectrum | Ref.* Page |
|---|---|---|
| 3355, 3326** | $\nu_a$ OH, N—H (ritonavir structure) | 94, 108, 143[1] |
| 3100, 3085, 3061, 3026** | $\nu$ (=CH ring phenyl), $\nu$ —C—H (thiazole) | 158[1], 301[2] |
| 2964, 2925, 2872** | $\nu_a$ and $\nu_s$, CH$_3$, —CH$_2$ | 50[1] |
| 1715 | $\nu$ Amide I, C=O | 153[1] |

TABLE 2-continued

Infrared Peaks for Amorphous Ritonavir Free Base[a]

| Observed MIR Absorption Band/ Range (cm$^{-1}$) at 4 cm$^{-1}$ resolution** | Assigned Functional Group(s) from the MIR Spectrum | Ref.* Page |
|---|---|---|
| 1623** | ν Amide II, C=O, ν  (—C=C— ring) | 154, 160[1] |
| 1526 | ν —C=N, ν —C=C—  | 216[3] |
| 1455** | ν$_a$ CH$_3$, Y$_b$ C—N—H | 52[1], 144[2] |
| 1385** | δ —C(CH$_3$)$_2$, ν$_{ip}$ —C=N, ν —C—S—C  , ν —C=C—  (ring),  | 52, 60[1], 303[2], 216[3] |
| 1334** | δ —C(CH$_3$)$_2$, δ —CH$_2$, —CH, Y$_ω$ —CH$_2$, —CH, ν —C—S—C  , ν —N—C—N | 51, 152[1], 303[2], 227[4] |
| 1241** | ν —C—N, C—O (coupled), δ  (—C—H ring), ν —C—O—C | 101, 154, 159[1] |
| 1134, 1094, 1064, 1053, 1023** | Y$_{b\,ip}$ C—H (ring), ν C-X (S), ν$_a$ C—O—C, ν —C—O | 154, 159[1], 216[3], 303[2] |
| 965, 882, 874, 791, 751, 702, 680** | δ$_{op}$ (ring), δ (ring C—H), ν C-X (S) | 160, 162, 163, 207[1] |

Peaks at 2541, 1961, and 1896 cm$^{-1}$, for example, are representative peaks from the IR spectrum of FIG. 3, i.e., amorphous ritonavir bis-hydrochloride. The representative peaks at 2541, 1961, and 1896 cm$^{-1}$ or a subset of those peaks, as well as the peaks shown in FIG. 3 or a subset of those peaks, may be used to characterize the amorphous ritonavir bis-hydrochloride of the invention.

4.5 Thermal DSC/TGA Characterization of Amorphous Ritonavir Bis-Hydrochloride

FIG. 5 shows a DSC of the large-scale amorphous ritonavir bis-hydrochloride. The sample started to degrade at about 105° C. and the Tg was about 90° C. (the sample was pre-dried at 90° C. for 2 minutes). The heat flow can be deconvoluted into two components, i.e., reversible heat flow (green curve) and irreversible heat flow (blue curve). The baseline of the reversible heat flow shows a step-wise change, which demonstrates the amorphous nature of the solid sample. The middle point of the baseline drop is defined as the glass transition temperature (Tg) of the amorphous solid. FIG. 6 shows a TGA of the large-scale amorphous ritonavir bis-hydrochloride. The amorphous solid showed about a 9% weight loss below 105° C., which suggested that the solid may be hygroscopic. The Hygroscopicity of the amorphous solid was confirmed by the moisture sorption data.

4.6 Moisture Sorption Characterization of Amorphous Ritonavir Bis-Hydrochloride A moisture sorption plot of the large-scale amorphous ritonavir bis-hydrochloride is shown in FIG. 7. The moisture sorption plot showed that the amorphous ritonavir bis-hydrochloride picked up about 20% (w/w) moisture at 90% RH (25° C.).

4.7 Solution $^{1}$H NMR and $^{13}$C NMR Characterization of Amorphous Ritonavir Bis-Hydrochloride A solution $^{1}$H NMR spectrum of the large-scale amorphous ritonavir bis-hydrochloride is shown in FIG. 8. The $^{1}$H NMR spectrum showed peaks corresponding to benzene rings, which suggests that the amorphous ritonavir bis-hydrochloride is not a degradant of ritonavir. A solution $^{13}$C NMR of the large-scale amorphous ritonavir bis-hydrochloride is shown in FIG. 9.

The following numbering scheme was used for the NMR assignments:

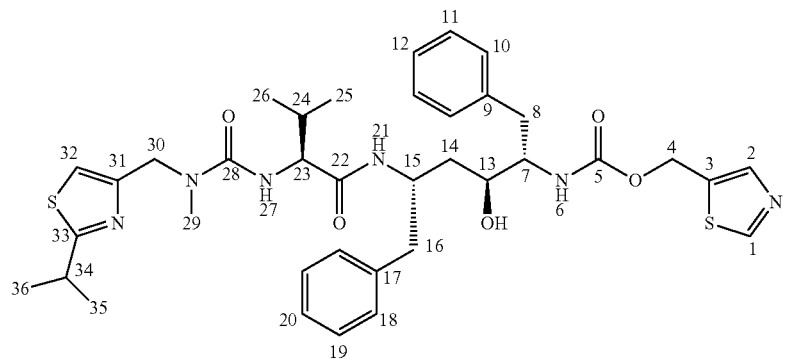

The $^{1}$H and $^{13}$C NMR assignments for ritonavir free base and ritonavir bis-hydrochloride are shown in Table 3.

TABLE 3

$^{1}$H and $^{13}$C NMR Assignments for Ritonavir Free Base and Ritonavir Bis-Hydrochloride

| Position | Group | $^{1}$H (ppm) ritonavir free base | $^{1}$H (ppm)$^a$ ritonavir bis-hydrochloride | $^{13}$C (ppm)$^b$ ritonavir free base | $^{13}$C (ppm)$^b$ ritonavir bis-hydrochloride |
|---|---|---|---|---|---|
| 1 | CH | 9.04 | 9.20 | 155.33 | 156.18 |
| 2 | CH | 7.85 | 7.92 | 142.92 | 141.63 |
| 3 | C | — | — | 134.00 | 134.84 |
| 4 | CH$_2$ | 5.14, 5.14 | 5.12 | 57.13 | 57.17 |
| 5 | C | — | — | 155.49 | 155.67 |
| 6 | NH | 6.84 | 6.91 | — | — |
| 7 | CH | 3.83 | 3.82 | 55.45 | 55.59 |
| 8 | CH$_2$ | 2.68 | 2.66 | 37.14 | 37.36 |
| 9 | C | — | — | 139.36 | 139.50 |
| 10 | CH | 7.19 | 7.19 | 128.91 | 129.07 |
| 11 | CH | 7.19 | 7.19 | 127.86 | 128.00 |
| 12 | CH | 7.14 | 7.15 | 125.69$^d$ | 125.84 |
| 13 | CH | 3.58 | 3.57 | 68.93 | 69.14 |
| 13 | OH | 4.59 | — | — | — |
| 14 | CH$_2$ | 1.46 | 1.45 | 38.23 | 38.51 |
| 15 | CH | 4.15 | 4.13 | 47.01 | 47.27 |
| 16 | CH$_2$ | 2.67, 2.61 | 2.60, 2.62 | 39.78 | 39.96 |
| 17 | C | — | — | 138.68 | 138.90 |
| 18 | CH | 7.12 | 7.10 | 129.19 | 129.35 |
| 19 | CH | 7.14 | 7.15 | 127.75 | 127.89 |
| 20 | CH | 7.14 | 7.08 | 125.63$^d$ | 125.78 |
| 21 | NH | 7.66 | 7.83 | — | — |
| 22 | C | — | — | 171.08 | 171.40 |
| 23 | CH | 3.94 | 3.89 | 59.45 | 60.00 |
| 24 | CH | 1.88 | 1.87 | 30.35 | 30.45 |
| 25 | CH$_3$ | 0.74 | 0.68$^c$ | 18.08$^e$ | 18.41$^f$ |
| 26 | CH$_3$ | 0.74 | 0.72$^c$ | 19.34$^e$ | 19.43$^f$ |
| 27 | NH | 5.99 | 6.12 | — | — |
| 28 | C | — | — | 157.38 | 157.52 |
| 29 | CH$_3$ | 2.87 | 2.88 | 34.44 | 34.68 |
| 30 | CH$_2$ | 4.46, 4.42 | 4.43, 4.51 | 48.20 | 47.83 |
| 31 | C | — | — | 152.74 | 151.70 |
| 32 | CH | 7.18 | 7.25 | 113.97 | 114.80 |
| 33 | C | — | — | 177.14 | 178.22 |
| 34 | CH | 3.23 | 3.28 | 32.38 | 32.20 |
| 35, 36 | CH$_3$ | 1.30 | 1.29 | 22.72 | 22.74 |

$^a$Relative to DMSO-d6 assigned to 2.50 ppm.
$^b$Relative to signal of DMSO assigned to 39.50 ppm.
$^c$Proton NMR assignments of H25 and H26 for ritonavir bis-hydrochloride may be interchangeable.
$^d$Carbon NMR assignments of C12 and C20 for ritonavir free base may be interchangeable.
$^e$Carbon NMR assignments of C25 and C26 for ritonavir free base may be interchangeable.
$^f$Carbon NMR assignments of C25 and C26 for ritonavir bis-hydrochloride may be interchangeable.

4.8 Polarized Light Microscopy of Large-scale Amorphous Ritonavir Bis-Hydrochloride The amorphous ritonavir bis-hydrochloride was examined using PLM. No ritonavir bis-hydrochloride particles with birefringence were observed for the large-scale amorphous ritonavir bis-hydrochloride at 100× magnification. At 200× and 500× magnification, the majority of ritonavir bis-hydrochloride particles were amorphous, but a few particles were found to have birefringence due to the edge of particles.

4.9 Solubility of Amorphous Ritonavir Bis-Hydrochloride Vs. Ritonavir

As discussed above, ritonavir free base has solubility in water of 1 μg/mL at pH 6.8, 37° C. See Law et al., "Physicochemical Considerations in the Preparation of Amorphous Ritonavir-Poly(ethylene-glycol) 8000 Solid Dispersions," J. Pharm. Sci. 90(8):1015-1025 (2001).

The solubility of the amorphous ritonavir bis-hydrochloride in water was determined to be 384 μg/mL.

4.10 Intrinsic Dissolution Rate (IDR) of Amorphous Ritonavir Bis-Hydrochloride and Ritonavir Free Base The IDR of amorphous ritonavir bis-hydrochloride and ritonavir free base was also evaluated. The amorphous ritonavir bis-hydrochloride showed a significantly faster dissolution rate than the ritonavir free base. See FIG. 10.

4.11 Effect of Salt Form on the Ritonavir Plasma Concentrations in Dogs

A series of studies evaluated the effect of the bis-hydrochloride and bis-tosylate form on the ritonavir plasma concentrations following single 100 mg base doses in dogs. Each of the salts was evaluated in a single group of six dogs. The free base and the two salts were weighed into gelatin capsules at a dose of 100 mg base for dosing in the dogs. The dogs were fasted overnight prior to dosing, but were permitted free access to water. Approximately 30 minutes prior to dosing, the dogs received a 100 ug/kg subcutaneous dose of histamine. Plasma concentrations of parent drug were determined by HPLC-MS/MS. The following formulations/salts were evaluated: amorphous ritonavir bis-hydrochloride, amorphous ritonavir free base, and ritonavir bis-tosylate.

Ritonavir plasma concentrations obtained from the amorphous free base were exceptionally low, with values below the limits of quantitation in two of the six animals. See FIG. 11. Mean peak plasma concentrations averaged only 5 ng/ml (range 0-10 ng/ml), with AUC values of 10 ng·hr/ml (range 0-22 ng·hr/ml). Plasma concentrations of ritonavir obtained from the 100 mg base oral dose of the ritonavir bis-tosylate were higher, with peak concentrations averaging 0.43 ug/ml (range 0.01-1.62 ug/ml) and AUC values of 1.40 ug·hr/ml (range 0.07-6.42 ug·hr/ml). Among the salts tested, the highest concentrations were obtained from the ritonavir bis-hydrochloride, with Cmax values of 3.16 ug/ml (range 1.16-8.39 ug/ml) and an AUC of 6.76 ug·hr/ml (range 3.16-20.2 ug·hr/ml). It should be noted that five of the six dogs provided AUC values in the ~3-7 ug·hr/ml, with only one dog at the higher end (20.2 ug·hr/ml).

The foregoing is merely illustrative of the invention and is not intended to limit the invention to the disclosed embodiments. Variations and changes which are obvious to one skilled in the art are intended to be within the scope and nature of the invention which are defined in the appended claims.

The claimed invention is:

1. A compound of (2S,3S,5S)-5-(N-(N-((N-methyl-N-((2-isopropyl-4-thiazolyl)-methyl)amino)carbonyl)-L-valinyl)amino)-2-(N-((5-thiazolyl)-methoxy-carbonyl)-amino)-1,6-diphenyl-3-hydroxyhexane bis-hydrochloride (ritonavir bis-hydrochloride), wherein said ritonavir bis-hydrochloride is amorphous.

2. The ritonavir bis-hydrochloride of claim 1, characterized by an IR spectrum having peaks at 2541, 1961, and 1896 $cm^{-1}$.

3. A process for the preparation of ritonavir bis-hydrochloride comprising:
dissolving ritonavir starting material in an ethyl acetate solution,
adding a hydrochloride gas/ethyl acetate solution into the ritonavir/ethyl acetate solution,
precipitating ritonavir bis-hydrochloride.

4. A pharmaceutical composition comprising a therapeutically effective amount of ritonavir bis-hydrochloride.

5. The pharmaceutical composition of claim 4, wherein at least 50% of ritonavir in said pharmaceutical composition is ritonavir bis-hydrochloride.

6. The pharmaceutical composition of claim 4, wherein at least 70% of ritonavir in said pharmaceutical composition is ritonavir bis-hydrochloride.

7. The pharmaceutical composition of claim 4, wherein at least 90% of ritonavir in said pharmaceutical composition is ritonavir bis-hydrochloride.

8. The pharmaceutical composition of claim 4, wherein at least 95% of ritonavir in said pharmaceutical composition is ritonavir bis-hydrochloride.

9. A method of inhibiting HIV protease comprising the step of administering to a patient in need thereof a therapeutically effective amount of ritonavir bis-hydrochloride.

10. The method of claim 9, wherein said ritonavir bis-hydrochloride is amorphous.

11. A method of enhancing the pharmacokinetics of a drug that is metabolized by cytochrome $P_{450}$ 3A4, comprising administering to a patient in need of such enhancement an effective amount of ritonavir bis-hydrochloride.

12. The method of claim 11, wherein said drug is an HIV protease inhibitor.

13. The method of claim 11, wherein said drug is an HCV protease inhibitor.

14. A process of making a pharmaceutical composition comprising ritonavir, said process comprising dissolving ritonavir bis-hydrochloride to form a solution.

15. The process of claim 14, wherein said ritonavir bis-hydrochloride is dissolved in a water-soluble polymer upon heating, and said process further comprises solidifying said solution.

16. The process of claim 14, wherein said ritonavir bis-hydrochloride is dissolved in a volatile solvent, and said process further comprises removing said solvent from said solution to form a powder.

17. A process of making a pharmaceutical composition comprising ritonavir, comprising mixing ritonavir bis-hydrochloride with one or more excipients and, optionally, one or more other drugs.

18. A composition of substantially pure ritonavir bis-hydrochloride containing less than 5% other ritonavir salts or forms.

* * * * *